US012655452B2

(12) United States Patent
Miasnikov et al.

(10) Patent No.: US 12,655,452 B2
(45) Date of Patent: Jun. 16, 2026

(54) METHODS AND COMPOSITIONS FOR ENHANCED ETHANOL PRODUCTION

(71) Applicant: DANISCO US INC., Palo Alto, CA (US)

(72) Inventors: Andrei Miasnikov, Union City, CA (US); Vivek Sharma, Fremont, CA (US)

(73) Assignee: Danisco US Inc., Palo Alto, CA (US)

( * ) Notice: Subject to any disclaimer, the term of this patent is extended or adjusted under 35 U.S.C. 154(b) by 880 days.

(21) Appl. No.: 17/791,095

(22) PCT Filed: Jan. 7, 2021

(86) PCT No.: PCT/US2021/012409

§ 371 (c)(1),
(2) Date: Jul. 6, 2022

(87) PCT Pub. No.: WO2021/142057

PCT Pub. Date: Jul. 15, 2021

(65) Prior Publication Data

US 2023/0044907 A1 Feb. 9, 2023

Related U.S. Application Data

(60) Provisional application No. 62/958,149, filed on Jan. 7, 2020.

(51) Int. Cl.
| | |
|---|---|
| *C12N 9/64* | (2006.01) |
| *C12N 9/24* | (2006.01) |
| *C12N 9/48* | (2006.01) |
| *C12N 9/58* | (2006.01) |
| *C12P 7/06* | (2006.01) |
| *C12P 7/10* | (2006.01) |

(52) U.S. Cl.
CPC . *C12P 7/10* (2013.01); *C12N 9/58* (2013.01)

(58) Field of Classification Search
CPC ..... C12P 7/06; C12P 7/10; C12N 9/58; C12N 9/48; C12N 9/2414
See application file for complete search history.

(56) References Cited

U.S. PATENT DOCUMENTS

| | | | |
|---|---|---|---|
| 3,912,590 A | 10/1975 | Slott et al. | |
| 4,933,279 A | 6/1990 | Carroll et al. | |
| 5,231,017 A | 7/1993 | Lantero et al. | |
| 2015/0175940 A1 | 6/2015 | Wells et al. | |
| 2015/0240223 A1* | 8/2015 | Hua | D06M 16/003 435/126 |
| 2020/0157581 A1* | 5/2020 | Hogsett | C12N 9/2414 |

FOREIGN PATENT DOCUMENTS

| | | | |
|---|---|---|---|
| CN | 105980552 A | | 9/2016 |
| CN | 108350444 A | | 7/2018 |
| CN | 108699573 A | | 10/2018 |
| CN | 110234751 A | | 9/2019 |
| WO | 92/20777 | | 11/1992 |
| WO | 03/066826 A2 | | 8/2003 |
| WO | 2007/145912 A1 | | 12/2007 |
| WO | 2010/008841 A2 | | 1/2010 |
| WO | 2015/066669 A1 | | 5/2015 |
| WO | 2015/078372 A1 | | 6/2015 |
| WO | 2016/065238 A1 | | 4/2016 |
| WO | 065238 | * | 4/2016 |
| WO | 2017/148389 A1 | | 9/2017 |
| WO | 2019/046232 A1 | | 3/2019 |

OTHER PUBLICATIONS

Johnston, David B. et al., Protease increases fermentation rate and ethanol yield in dry-grind ethanol production, Bioresource Technology, 2014, pp. 18-25, vol. 154.
Nomenclature Committee of the International Union of Biochemistry and Molecular Biology (NC-IUBMB), European Journal of Biochemistry, 1994, pp. 1-5, vol. 223.
Nomenclature Committee of the International Union of Biochemistry and Molecular Biology (NC-IUBMB), European Journal of Biochemistry, Supplement 2, 1995, pp. 1-6, vol. 232.
Nomenclature Committee of the International Union of Biochemistry and Molecular Biology (NC-IUBMB), European Journal of Biochemistry, Supplement 3, 1996, pp. 1-5, vol. 237.
Nomenclature Committee of the International Union of Biochemistry and Molecular Biology (NC-IUBMB), European Journal of Biochemistry, Supplement 4, 1997, pp. 1-6, vol. 250.
Nomenclature Committee of the International Union of Biochemistry and Molecular Biology (NC-IUBMB), European Journal of Biochemistry, Supplement 5, 1999, pp. 610-650, vol. 264.
International Search Report and Written Opinion—PCT/US2021/012409—mailed May 7, 2021.
Lee, Byung Rho et al., Aorsin, a novel serine proteinase with trypsin-like specificity at acidic pH, Biochem. J, 2003, pp. 541-548, vol. 371.
Translated Chinese Office Action dated Apr. 17, 2025 that includes Chinese Search Report—CN Application No. Appl No. 202180018619.3.

* cited by examiner

*Primary Examiner* — Maryam Monshipouri

(57) ABSTRACT

The instant disclosure is generally related to microbial fermentation, grain processing and ethanol production. Certain embodiments of the disclosure are therefore related to starch-containing materials and the microbial fermentation of such starch-containing materials for the production ethanol. More particularly, certain embodiments are related to novel protease mixtures for use in processing such starch-containing materials in starch to ethanol fermentation processes described herein.

4 Claims, 1 Drawing Sheet

Specification includes a Sequence Listing.

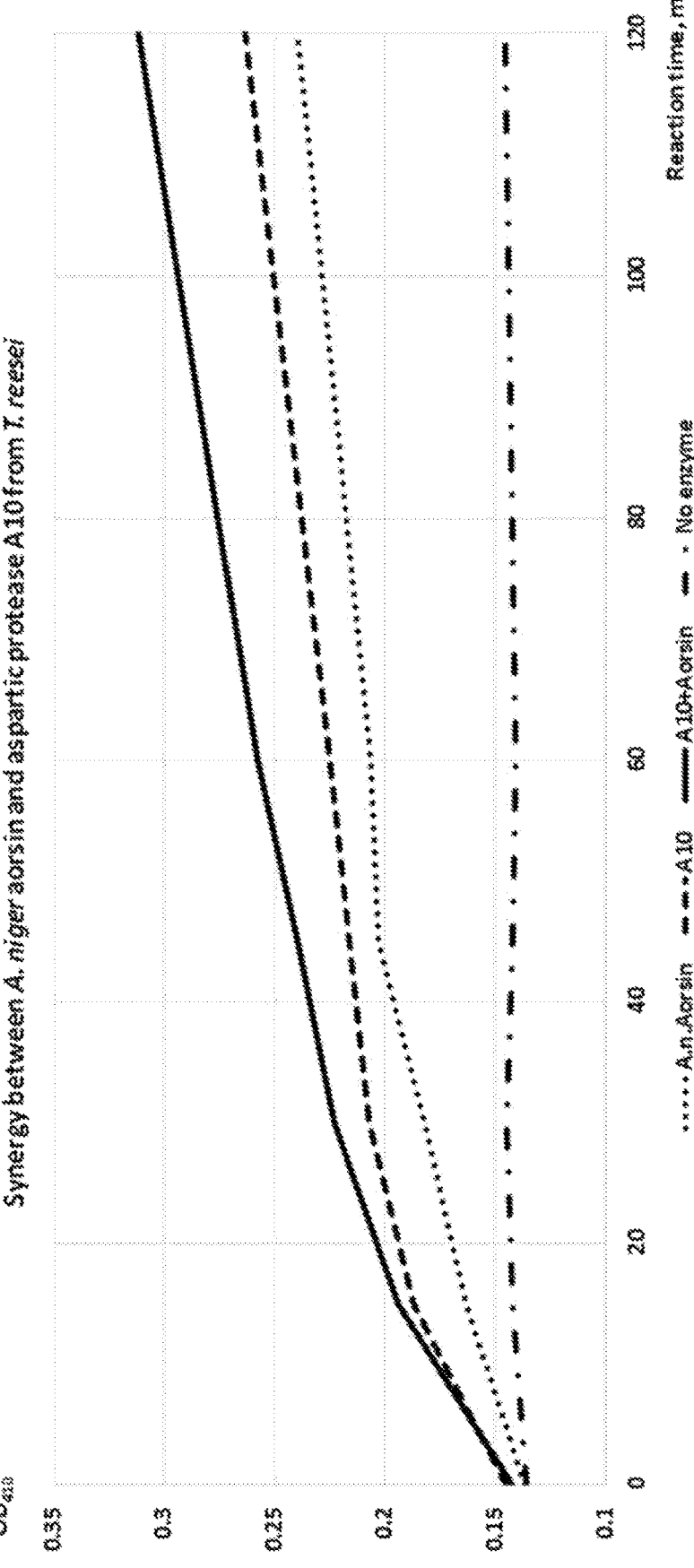

METHODS AND COMPOSITIONS FOR ENHANCED ETHANOL PRODUCTION

CROSS REFERENCE TO RELATED APPLICATIONS

This application claims benefit to International Patent Application PCT/US2021/012409, filed Jan. 7, 2021, which claims the benefit of U.S. Provisional Patent Application No. 62/958,149, filed Jan. 7, 2020, which are incorporated by reference in their entirety.

TECHNICAL FIELD

The present disclosure is generally related to the fields of biology, molecular biology, genetics, microbial fermentation, grain processing, ethanol production and the like. Certain embodiments of the disclosure are related to starch-containing materials (feedstocks) and microbial fermentation thereof for the biological production ethanol.

REFERENCE TO A SEQUENCE LISTING

The contents of the electronic submission of the text file Sequence Listing, named "NB41362-WO-PCT_Sequence-Listing.txt" was created on Dec. 7, 2020 and is 20 KB in size, which is hereby incorporated by reference in its entirety.

BACKGROUND OF INVENTION

A number of agricultural crops are viable candidates for the conversion of starch to fermentable feedstocks, wherein such fermentable feedstocks can be fed to various microbes to produce a variety of biochemicals (e.g., ethanol). Typically, corn is used as the primary starch source for producing such fermentable feedstocks, although other high-starch content sources like sorghum, wheat, barley, rye, cassava and the like are beginning to gain more attention as viable feedstocks for the industrial production of biochemicals. The biological production of ethanol from starch-containing materials (feedstocks) is generally well known in the art.

For example, a method known in the art as a "conventional" process is commonly used for producing a fermentable feedstock from insoluble starch, which generally involves heating whole ground grain (or a starch slurry) to temperatures in excess of 95° C. in the presence of alpha-amylase (a process known as "liquefaction"), followed by cooling, pH adjustment, and subsequent glucoamylase hydrolysis (a process known as "saccharification"), wherein such conventional process can produce fermentable feed stocks containing, e.g., greater than 90% glucose (e.g., see U.S. Pat. Nos. 3,912,590; 4,933,279). Another well-known process, often referred to as "raw starch hydrolysis" (or "granular starch hydrolysis"), includes simultaneously saccharifying and fermenting granular starch below the initial gelatinization temperature, typically in the presence of an acid fungal alpha-amylase and a glucoamylase (e.g. see PCT Publication Nos. WO1992/20777, WO2003/66826 and WO2007/145912).

Although such processes for the biological production of ethanol from starch-containing materials (feedstocks) are generally known, there remain ongoing and unmet needs in the art, including, but not limited to, methods for increasing the amount of ethanol produced in such processes (e.g., increased yield of recovered ethanol), methods for increasing the rate of ethanol production, methods for reducing the amount of glycerol produced, methods that improve the ability of an ethanol production host cell to ferment, and the like.

SUMMARY OF THE INVENTION

The present disclosure is generally related to the methods and compositions for the biological production of ethanol. Certain embodiments are related to ethanol producing microbial cells (strains) and their use in fermentation processes therefor. Certain embodiments are related to compositions and methods for producing ethanol in a starch to ethanol fermentation process. Certain other embodiments are related to compositions and methods for enhancing the rate of ethanol production in a starch to ethanol fermentation process. Other embodiments are related to compositions and methods for reducing the amount of glycerol produced in a starch to ethanol fermentation process. Certain other embodiments are related to identifying protease mixtures (combinations) that can increase the ethanol yield, and/or increase the rate of ethanol production, and/or reduce the amount of glycerol produced in a starch to ethanol fermentation processes, wherein the protease mixtures (combinations) can be added during saccharification and/or fermentation, or are present during saccharification and/or fermentation.

Certain other embodiments are related to compositions and methods that improve the ability of an ethanol production host cell to ferment starch compositions in a starch to ethanol fermentation processes, wherein the protease mixtures (combinations) can be added during saccharification and/or fermentation, or are present during saccharification and/or fermentation.

In certain embodiments, the disclosure is therefore related to methods for producing ethanol from a starch-containing material comprising (a) liquefying a starch-containing material at a temperature above the initial gelatinization temperature of the starch-containing material in the presence of an alpha-amylase, (b) saccharifying the liquefied material obtained in step (a) using a saccharifying enzyme, and (c) fermenting the material obtained in step (b) with an ethanol production host under suitable conditions for the production of ethanol, wherein step (b) and/or step (c) is performed in the presence of an aspartic and serine protease mixture.

In certain embodiments of the methods, the saccharification and fermentation are performed simultaneously. In other embodiments of the methods, the ethanol produced is recovered.

In other embodiments of the methods, the amount of ethanol produced is increased relative to amount of ethanol produced using the same method except for wherein step (b) and/or step (c) is performed in the presence of aspartic protease, or a serine protease, but not a mixture thereof. In certain other embodiments of the methods, the rate of ethanol production is increased relative to the rate of ethanol production using the same method except for wherein step (b) and/or step (c) is performed in the presence of aspartic protease, or a serine protease, but not a mixture thereof. In another embodiment of the methods, the amount of glycerol produced is reduced relative to the amount of glycerol produced using the same method except for wherein step (b) and/or step (c) is performed in the presence of aspartic protease, or a serine protease, but not a mixture thereof. In other embodiments, the ethanol production host requires a reduced amount supplemented nitrogen relative to the same ethanol production host fermented using the same method except for wherein step (b) and/or step (c) is performed in the presence of aspartic protease, or a serine protease, but not a mixture thereof. In certain embodiments, the aspartic protease comprises about 60% sequence identity to the aspartic protease of SEQ ID NO: 2 or SEQ ID NO: 6 and the serine protease comprises about 60% sequence identity to the serine protease of SEQ ID NO: 4.

In other embodiments, the disclosure is directed to methods for producing ethanol from a starch-containing material comprising (a) saccharifying a starch-containing material at a temperature below the initial gelatinization temperature of the starch-containing material using a saccharifying enzyme, and (b) fermenting the material obtained is step (a) with an ethanol production host under suitable conditions for the production of ethanol, wherein step (a) and/or step (b) is performed in the presence of an aspartic and serine protease mixture. In certain embodiments of the methods, the amount of ethanol produced is increased relative to amount of ethanol produced using the same method except for wherein step (a) and/or step (b) is performed in the presence of aspartic protease, or a serine protease, but not a mixture thereof. In other embodiments of the methods, the rate of ethanol production is increased relative to the rate of ethanol production using the same method except for wherein step (a) and/or step (b) is performed in the presence of aspartic protease, or a serine protease, but not a mixture thereof. In yet other embodiments, the amount of glycerol produced is reduced relative to the amount of glycerol produced using the same method except for wherein step (a) and/or step (b) is performed in the presence of aspartic protease, or a serine protease, but not a mixture thereof. In certain other embodiments of the methods, the ethanol production host requires a reduced amount supplemented nitrogen relative to the same ethanol production host fermented using the same method except for wherein step (a) and/or step (b) is performed in the presence of aspartic protease, or a serine protease, but not a mixture thereof. In other embodiments, the aspartic protease comprises about 60% sequence identity to the aspartic protease of SEQ ID NO: 2 or SEQ ID NO: 6 and the serine protease comprises about 60% sequence identity to the serine protease of SEQ ID NO: 4.

Thus, in certain other embodiments, the disclosure is related to methods for producing ethanol from a starch-containing material comprising fermenting a starch-containing material with an ethanol production host under suitable conditions for the production of ethanol, wherein the ethanol production host expresses and secretes a heterologous aspartic protease and a heterologous serine protease, and recovering the ethanol produced.

Certain other embodiments of the disclosure are therefore directed to a protease composition comprising a mixture of an aspartic protease and a serine protease. In preferred embodiments, the protease composition comprising a mixture of an aspartic protease and a serine protease is used in the biological production of ethanol from a starch-containing material. Thus, in certain embodiments, the aspartic protease comprises about 60% sequence identity to the aspartic protease of SEQ ID NO: 2 or SEQ ID NO: 6 and the serine protease comprises about 60% sequence identity to the serine protease of SEQ ID NO: 4. In certain other embodiments, the serine protease excludes enzymes designated EC 3.4.14 and/or the serine protease excludes enzymes designated EC 3.4.16. In certain embodiments, the protease composition of is admixed with a starch-containing material. In another embodiment, the protease composition is admixed with a starch-containing material after liquefying the starch-containing material. In yet other embodiments, the protease composition is admixed with a granular starch composition obtained from a starch-containing material. In other embodiments, the protease composition is admixed with a starch-containing material in a simultaneous saccharification and fermentation (SSF) process.

BRIEF DESCRIPTION OF THE BIOLOGICAL SEQUENCES

SEQ ID NO: 1 is a *T. reesei* polynucleotide sequence encoding an A10 aspartic protease comprising SEQ ID NO: 2.

SEQ ID NO: 2 is the amino acid sequence if the A10 aspartic protease encoded by SEQ ID NO: 1.

SEQ ID NO: 3 is an *A. niger* polynucleotide sequence encoding an aorsin serine protease comprising SEQ ID NO: 4.

SEQ ID NO: 4 is the amino acid sequence if the aorsin serine protease encoded by SEQ ID NO: 3.

SEQ ID NO: 5 is a *T. reesei* polynucleotide sequence encoding an aspartic protease (Fermgen®) of SEQ ID NO: 6.

SEQ ID NO: 6 is the amino acid sequence of the Fermgen® aspartic protease.

BRIEF DESCRIPTION OF THE DRAWINGS

FIG. 1 shows hydrolytic synergy of a 50 μg/ml combination of an aspartic (A10) protease (25 μg/ml) and serine (aorsin) protease (25 μg/ml) relative to the hydrolytic activity of the aspartic (A10) protease (50 μg/ml) alone, or the serine (aorsin) protease (50 μg/ml) alone.

DETAILED DESCRIPTION

As set forth and described herein, the present compositions and methods of the disclosure are generally related to the biological production of ethanol. Certain embodiments are related to ethanol producing microbial cells (strains) and their use in fermentation processes therefor. Certain embodiments are related to compositions and methods for producing ethanol in a starch to ethanol fermentation process. Certain other embodiments are related to compositions and methods for enhancing the rate of ethanol production in a starch to ethanol fermentation process. Other embodiments are related to compositions and methods for reducing the amount of glycerol produced in a starch to ethanol fermentation process. Certain other embodiments are related to identifying protease mixtures (combinations) that can increase the ethanol yield, and/or increase the rate of ethanol production, and/or reduce the amount of glycerol produced in a starch to ethanol fermentation processes, wherein the protease mixtures (combinations) can be added during saccharification and/or fermentation, or are present during saccharification and/or fermentation. Certain other embodiments are related to compositions and methods that improve the ability of an ethanol production host cell to ferment starch compositions in a starch to ethanol fermentation processes, wherein the protease mixtures (combinations) can be added during saccharification and/or fermentation, or are present during saccharification and/or fermentation.

More particularly, as described and exemplified herein, a seminal finding of the instant disclosure is that the combined use of an aspartic acid protease and a serine protease mixture (combination) during a starch to ethanol fermentation process increases the ethanol yield, with a concomitant reduction in the amount of glycerol produced. Furthermore, as described and exemplified herein, the use of such combined aspartic and serine protease mixtures during starch to ethanol fermentation processes were observed to increase the rate at which the increased ethanol yields were obtained. In addition, or alternatively, a further finding of the instant disclosure is that the combined use of such aspartic and serine protease mixtures during a starch to ethanol fermentation process improves the ability of the ethanol production host cell to ferment. For example, without wishing to be bound by theory or mechanism, it is believed that the novel aspartic and serine protease mixtures present, or added during a starch to ethanol fermentation processes increase the concentration of peptides and free amino acids present in a feedstock, which peptides and free amino acids are contemplated to be an excellent amine nitrogen source and/or energy source and/or nutrient source for the ethanol production host, as presented and described herein.

I. DEFINITIONS

Prior to describing the present compositions and methods in detail, the following terms are defined for clarity. Terms not defined should be accorded their ordinary meanings as used in the relevant art. Unless defined otherwise, all technical and scientific terms used herein have the same meaning as commonly understood by one of ordinary skill in the art to which the present compositions and methods apply.

All publications and patents cited in this specification are herein incorporated by reference.

Where a range of values is provided, it is understood that each intervening value, to the tenth of the unit of the lower limit unless the context clearly dictates otherwise, between the upper and lower limit of that range and any other stated or intervening value in that stated range, is encompassed within the present compositions and methods. The upper and lower limits of these smaller ranges may independently be included in the smaller ranges and are also encompassed within the present compositions and methods, subject to any specifically excluded limit in the stated range. Where the stated range includes one or both of the limits, ranges excluding either or both of those included limits are also included in the present compositions and methods.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. For example, in connection with a numerical value, the term "about" refers to a range of −10% to +10% of the numerical value, unless the term is otherwise specifically defined in context. In another example, the phrase a "pH value of about 6" refers to pH values of from 5.4 to 6.6, unless the pH value is specifically defined otherwise.

The headings provided herein are not limitations of the various aspects or embodiments of the present compositions and methods which can be had by reference to the specification as a whole. Accordingly, the terms defined immediately below are more fully defined by reference to the specification as a whole.

In accordance with this Detailed Description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

It is further noted that the claims may be drafted to exclude any optional element. As such, this statement is intended to serve as antecedent basis for use of such exclusive terminology as "solely", "only", "excluding", "not including" and the like in connection with the recitation of claim elements, or use of a "negative" limitation.

It is further noted that the term "comprising", as used herein, means "including, but not limited to", the component(s) after the term "comprising". The component(s) after the term "comprising" are required or mandatory, but the composition comprising the component(s) may further include other non-mandatory or optional component(s).

It is also noted that the term "consisting of," as used herein, means "including and limited to", the component(s) after the term "consisting of". The component(s) after the term "consisting of" are therefore required or mandatory, and no other component(s) are present in the composition.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

As used herein, the term "ethanol" refers to ethanol produced as a result of a biological fermentation process.

As used herein, the phrase "recovering ethanol" refers to the purification and/or isolation of ethanol. Suitably, the recovery results in ethanol that is substantially free of other components (e.g. contaminants). Therefore, the recovery may result in an alcohol that is at least about 90% pure, suitably at least about 95% pure, more suitably at least 99% pure. Preferably the recovery may result in an alcohol that is at least about 99.9% pure.

As used herein, the term "Enzyme Commission" Number, abbreviated "EC", refers to enzyme nomenclature recommendations of the Nomenclature Committee of the International Union of Biochemistry and Molecular Biology (NC-IUBMB), as generally known to one skilled in the art (e.g., see enzyme nomenclature from NC-IUBMB, 1992 (Academic Press, San Diego, California), including supplements 1-5 published in 1994 (Eur. J. Biochem., 223:1-5), 1995 (Eur. J. Biochem. 232:1-6); 1996 (Eur. J. Biochem. 237:1-5), 1997 (Eur. J. Biochem. 250:1-6) and 1999 (Eur. J. Biochem. 264:610-650), respectively. Likewise, the nomenclature is regularly supplemented and updated.

As used herein, the term "protease" includes any enzyme belonging to the EC 3.4 enzyme group (including each of the eighteen subclasses thereof). As described herein, proteins (polypeptides) having protease activity (i.e., proteases), are also known in the art as peptidases, proteinases, peptide hydrolases, and proteolytic enzymes.

As used herein, proteases may be of the "exo-type" (i.e., exopeptidases) that hydrolyze proteins (peptide bonds) starting at either N-terminal or C-terminal end of the protein chain, or of the "endo-type" (i.e., endopeptidases) that hydrolyze peptide bonds of the non-terminal ends of the protein chain (i.e., internal peptide bonds).

As used herein, the terms "aspartic acid" protease and "aspartic" protease are used interchangeably, and refer to any protein (enzyme) belonging to the EC 3.4.23 aspartic acid proteases. In general, aspartic proteases are endopeptidases comprising two (2) highly conserved aspartate residues in the active site, and are optimally active at acidic pH.

As used herein, "Fermgen®" acid fungal proteases refer to one of multiple aspartic proteases (e.g., EC 3.4.23) obtained via controlled fermentation of *T. reesei* fungal strains. An exemplary Fermgen® polynucleotide sequence encoding a Fermgen® protease are set forth in SEQ ID NO: 5 and SEQ ID NO: 6, respectively.

Serine proteases of the peptidase family S53 comprise several types of peptidases, including serine carboxypeptidases (EC 3.4.16), the tripeptidyl aminopeptidases (exotype) and serine endopeptidases (Rawlings and Barrett, 1993).

As used herein, the term "serine" protease may refer to any protein (enzyme) belonging to the EC 3.4.21 serine proteases.

In certain embodiments, term "serine" protease includes proteins (enzymes) belonging to the EC 3.4.14 group (e.g., exopeptidases such as dipeptidyl-peptidase I, dipeptidyl-peptidase II, tripeptidyl-peptidase I, tripeptidyl-peptidase II, and the like) and/or belonging to the EC 3.4.16 group (e.g., serine-type carboxypeptidases such as serine-type D-Ala-D-Ala carboxypeptidase, carboxypeptidase C and the like).

In certain embodiments, term "serine" protease excludes proteins (enzymes) belonging to the EC 3.4.14 group.

In certain other embodiments, a "serine" protease excludes "serine-type carboxypeptidases" of EC 3.4.16.

As used herein, the name "aorsin" refers to a serine protease from *Aspergillus oryzae* (Lee et al. Biochem 2003), and homologs thereof from other fungal species comprising at least about 40%, 50%, 60%, 70%, 80%, 90%, 91%-99% sequence identity with *A. oryzae* (aorsin) enzyme.

As used herein, the name "sedolisin" refers to a serine-type carboxypeptidase of EC 3.4.16.

As used herein, the term "protease activity" means proteolytic activity (EC 3.4). Protease activity can generally be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12 and examples of assay-temperatures are 15° C., 20° C., 25° C., 30° C., 35° C., 37° C., 40° C., 45° C., 50° C., 55° C., 60° C., 65° C., 70° C., 80° C., 90° C., or 95° C. Examples of general protease substrates are casein, bovine serum albumin (BSA) and hemoglobin.

As used herein, "fermentable sugar(s)" refer to saccharides that are capable of being metabolized under fermentation conditions. These fermentable sugars typically refer to glucose, maltose and maltotriose. In some embodiments sucrose, galactose, xylose, arabinose etc. may also be a fermentable sugar. Suitably, fermentable sugars may be obtained by the hydrolysis of starch and other polysaccharide compositions (e.g., feedstocks).

As used herein, the term "feedstock" refers to a composition comprising at least one of the following: starch, cellulose, hemicellulose, lignocellulose, fermentable sugars or a combination thereof. The feedstock may be a starch, a grain-based material (e.g., a cereal, wheat, barley, rye, rice, triticale, millet, milo, sorghum or corn), a tuber (e.g., potato or cassava), a root, a sugar (e.g., cane sugar, beet sugar, molasses or a sugar syrup), stillage, wet cake, DDGS, cellulosic biomass, hemicellulosic biomass, a whey protein, soy based material, lignocellulosic biomass or combinations thereof.

As used herein, a "fraction of a feedstock" refers to any component of a feedstock that is separated out during the processing of the feedstock.

As used herein, "starch" refers to any material comprised of the complex polysaccharide carbohydrates of plants, comprised of amylose and amylopectin with the formula $(C_6H_{10}O_5)x$, wherein "x" can be any number. In particular, "starch" refers to any plant-based material including, but not limited to grains, cereals, grasses, tubers and roots, and more particularly wheat, barley, corn, rye, rice, sorghum, brans, cassava, millet, potato, sweet potato, and tapioca.

As used herein, a "starch-containing material" includes starch-containing materials derived from barley, beans, cassava, cereals, corn, milo, peas, potatoes, rice, rye, sago, sorghum, sweet potatoes, tapioca, wheat, and whole grains, or any mixture thereof. In certain embodiments, a starch-containing material is a granular starch composition. In other embodiments, the starch-containing material is derived from whole grain. The starting material is generally selected based on the desired fermentation product. The starch-containing material may also be a waxy or non-waxy type of corn and barley. In a particular embodiment the starch-containing material is derived from corn. In another embodiment the starch-containing material is derived from wheat.

The phrase "granular starch" refers to uncooked (raw) starch, which has not been subject to gelatinization, where "starch gelatinization" means solubilization of starch molecules to form a viscous suspension.

As used herein, "hydrolysis of starch" and the like refers to the cleavage of glycosidic bonds with the addition of water molecules. Thus, enzymes having "starch hydrolysis activity" catalyze the cleavage of glycosidic bonds with the addition of water molecules.

In certain embodiments, a starch-containing material (feedstock) may be subjected to one or more processing steps either before, during or after fermentation. As used herein, the phrase "one or more processing steps" includes, but is not limited to, a milling, cooking, liquefaction, saccharification, fermentation, and simultaneous saccharification and fermentation (SSF).

As used herein, the term "initial gelatinization temperature" means the lowest temperature at which starch gelatinization commences.

As used herein, the term "milling" refers to any milling of a feedstock, including wet milling, dry grinding, or combinations thereof. Milling refers to a process which aids in breaking up the raw material used for the preparation of the feedstock into appropriately sized particles to facilitate downstream processing of the feedstock (e.g., to facilitate the cooking process).

As used herein, "wet milling" is a process of milling that requires wet steeping of the feedstock (e.g., corn kernel) before processing. Wet steeping is then followed by a series of unit operations carried out in order to recover starch. The grain is typically soaked or "steeped" in water with dilute sulfurous acid for 24 to 48 hours prior to being subjected to a series of grinders. The downstream processes may include removal of oil (e.g., corn oil) followed by further stages to separate out fiber, protein (e.g., gluten) and starch components (e.g., such as the endosperm). This may be achieved by centrifugation, use of screens and hydroclonic separators. The starch and water remaining from this process may then be subjected to fermentation.

As used herein, "dry grinding" refers to a process in which a starting material, such as a grain, is ground into a flour (e.g., meal) before further processing. Generally, the flour is then slurried with water to form a mash (slurry) prior to being processed in downstream steps (e.g., saccharification). Ammonia is typically added to the mash and serves to both control the pH and provide a nutrient source to the ethanol production host used in fermentation. Thus, in certain embodiments, dry grinding is used during processing of a feedstock (or a fraction thereof).

Suitably, a starch-containing material (feedstock) obtained after milling or dry grinding may be subjected to liquefaction and/or saccharification and/or fermentation and/ or simultaneous saccharification and fermentation (herein, "SSF"). This may be with or without a cooking step (e.g., after milling and before either liquefaction or saccharification).

In certain embodiments, the starch-containing material (feedstock) is subjected to cooking. Typically, the cooking process may take place post-milling. Suitably the cooking process may take place at 90° C.-120° C. Suitably the cooking may be carried out prior to liquefaction and/or saccharification. Suitably the cooking process may reduce bacteria levels prior to fermentation. In some embodiments, one or more enzymes may be added at this stage or thereafter. Suitably, a-amylase may be added following the cooking process (e.g., in a liquefaction process).

In other embodiments starch-containing material (feedstock) is not subjected to cooking. In such an embodiment, saccharification and fermentation, or SSF may be carried out on the feedstock (or fraction thereof) comprising granular or raw starch (e.g., starch that has been treated at temperatures below gelatinization of the starch).

As used herein, the term "liquefaction" refers to a process in which the starch is liquefied, usually by increasing the temperature. Liquefaction of the starch results in a significant increase in viscosity. For this reason, amylases may be introduced in order to reduce the viscosity. The temperature at which the starch liquefies varies depending upon the source of the starch.

Starch processing can also be carried at temperatures from about 25° C. to just below the liquefaction temperature. These types of processes are often referred to as "granular starch hydrolysis", "direct starch hydrolysis", "raw starch hydrolysis", "low temperature starch hydrolysis" and the like. In some cases, the starch is pretreated at temperatures below the liquefaction temperatures in order to enhance enzymatic hydrolysis and/or other processes for treatment of starch.

In other embodiments, liquefaction may be carried out at a lower temperature and/or a "cold cook process" that does not involve complete liquefaction of starch.

The starch-containing material (feedstock) may also undergo saccharification. The saccharification may be separate to fermentation, or simultaneously therewith. Separate saccharification and fermentation is a process whereby starch present in a feedstock or a fraction thereof is converted to glucose and subsequently an ethanol production host converts the glucose into ethanol.

As used herein, "simultaneous saccharification and fermentation" or "SSF" is a process whereby starch present in a starch-containing material (feedstock) is converted to glucose and, at the same time and in the same reactor, an ethanol production host converts the glucose into ethanol. In some embodiments, saccharification may be carried out at low temperatures As used herein, the terms "saccharifying enzyme" or "saccharifying enzymes" include, but are not limited to "a-amylases (EC 3.2.1.1), glucoamylases (EC 3.2.1.3), iso-amylases (EC 3.2.1.68), B-amylases (EC 3.2.1.2), pullulanases (EC 3.2.1.41), endoglucanases (EC 3.2.1.4), cellobiohydrolases (EC 3.2.1.91), B-glucosidases (E.C. 3.2.1.21), cellulases (EC 3.2.1.74), lichenases (EC 3.1.1.73), lipases (EC 3.1.1.3), lipid acyltransferases (generally classified as EC 2.3.1.x), phospholipases (EC 3.1.1.4, E.C. 3.1.1.32, or EC 3.1.1.5), phytases (e.g., 6-phytase (EC 3.1.3.26) or a 3-phytase (EC 3.1.3.8), xylanases (e.g., endo-1,4-B-d-xylanase (EC 3.2.1.8) or 1,4 B-xylosidase (EC 3.2.1.37) or EC 3.2.1.32, EC 3.1.1.72, EC 3.1.1.73), glucoamylases (EC 3.2.1.3), hemicellulases (e.g., xylanases), or a keratinase (EC 3.4.x.x)), debranching enzymes, cutinases, esterases and/or mannanases (e.g., a B-mannanase (EC 3.2.1.78)) transferases, glucosidases, and arabinofuranosidase.

As used herein, the term "admixing" refers to the mixing of one or more ingredients and/or enzymes, where the one or more ingredients or enzymes are added in any order and in any combination. Suitably, admixing may relate to mixing one or more ingredients and/or enzymes simultaneously or sequentially.

As used herein, the phrases "ethanol production host", "ethanol producing host", "ethanol producing host cell" and the like may be used interchangeably, and include any microorganism that has the ability to ferment a fermentable sugar source to produce ethanol.

In certain embodiments, an ethanol production host is a yeast. Suitably the yeast may be selected from the group consisting of *Saccharomyces*, *Kluyveromyces*, *Zygosaccharomyces*, *Issatchenkia*, *Kazachstania* and *Torulaspora*. In yet another embodiment, an ethanol producing organism may be a bacterium (e.g., *Zymomonas*, *Escherichia*, etc.).

In certain embodiments, an ethanol production host (e.g., yeast) is added before, during, or after adding an aspartic and serine protease composition to a starch-containing material (feedstock).

As used herein, a "lignocellulosic biomass" may comprise cellulose, hemicellulose and the aromatic polymer lignin. Hemicellulose and cellulose (including insoluble arabinoxylans) by themselves are also potential energy sources, as they consist of C5- and C6-saccharides.

Suitably the lignocellulosic biomass may be any cellulosic, hemicellulosic or lignocellulosic material, for example agricultural residues, bioenergy crops, industrial solid waste, municipal solid waste, sludge from paper manufacture, yard waste, wood waste, forestry waste and combinations thereof. The lignocellulosic biomass may be selected from the group consisting of corn cobs, crop residues such as corn husks, corn gluten meal (CGM), corn stover, corn fiber, grasses, beet pulp, wheat straw, wheat chaff, oat straw, wheat middlings, wheat shorts, rice bran, rice hulls, wheat bran, oat hulls, wet cake, Distillers Dried Grain (DDG), Distillers Dried Grain Solubles (DDGS), palm kernel, citrus pulp, cotton, lignin, barley straw, hay, rice straw, rice hulls, switchgrass, *miscanthus*, cord grass, reed canary grass, waste paper, sugar cane bagasse, sorghum bagasse, forage sorghum, sorghum stover, soybean stover, soy, components obtained from milling of trees, branches, roots, leaves, wood chips, sawdust, shrubs and bushes, vegetables, fruits and flowers.

Wet-cake, Distillers Dried Grains and Distillers Dried Grains with Solubles are products obtained after the removal of ethanol by distillation from fermentation of a grain or a grain mixture by methods employed in the grain distilling industry. Stillage coming from the distillation (e.g., comprising water, remainings of the grain, yeast cells, etc.) is separated into a "solid" part and a "liquid" part. The solid part is called "wet-cake" and can be used as animal feed as such. The liquid part is (partially) evaporated into a syrup (solubles). The liquid part is often referred to as the thin stillage. When the wet-cake is dried it is Distillers Dried Grains (DDG). When the wet-cake is dried together with the syrup (solubles) it is Distillers Dried Grans with Solubles (DDGS).

As used herein, the term "expression" includes any step involved in the production of a polypeptide including, but not limited to, transcription, post-transcriptional modification, translation, post-translational modification, and secretion.

As used herein, the term "expression vector" means a linear or circular DNA molecule that comprises a polynucleotide encoding a polypeptide and is operably linked to control sequences that provide for its expression.

II. BIOLOGICAL PRODUCTION OF ETHANOL FROM STARCH-CONTAINING MATERIALS

As generally described above, certain aspects of the instant disclosure are related to improved methods/processes for producing ethanol from starch-containing materials by the combined use of at least one aspartic acid protease and at least one serine protease described herein. For example, certain embodiments are related to methods for producing ethanol from a starch-containing material comprising (a) saccharifying a starch-containing material at a temperature below the initial gelatinization temperature of the starch-containing material using a saccharifying enzyme, and (b) fermenting the material obtained in step (a) with an ethanol production host (under suitable conditions for the production of ethanol), wherein step (a) and/or step (b) is/are performed in the presence of an aspartic and serine protease mixture.

In another embodiment, a method for producing ethanol from a starch-containing material comprises (a) liquefying a starch-containing material at a temperature above the initial gelatinization temperature of the starch-containing material in the presence of an alpha-amylase, (b) saccharifying the liquefied material obtained in step (a) using a saccharifying enzyme, and (c) fermenting the material obtained in step (b) with an ethanol production host (under suitable conditions for the production of ethanol), wherein step (b) and/or step (c) is performed in the presence of an aspartic and serine protease mixture.

As set forth in the Background section, methods/processes for producing ethanol from starch-containing materials are generally well known. The "conventional process" includes liquefying gelatinized starch at high temperature using typically a bacterial alpha-amylase, followed by simultaneous saccharification and fermentation carried out in the presence of a glucoamylase and a fermenting organism. The "raw starch hydrolysis" process includes simultaneously saccharifying and fermenting granular starch below the initial gelatinization temperature, typically in the presence of an acid fungal alpha-amylase and a glucoamylase.

For example, native starch consists of microscopic granules, which are insoluble in water at room temperature. When an aqueous starch slurry is heated, the granules swell and eventually burst, dispersing the starch molecules into the solution. At temperatures up to about 50° C. to 75° C., the swelling may be reversible. However, with higher temperatures, an irreversible swelling called "gelatinization" begins. During "gelatinization" there is a dramatic increase in viscosity.

Granular starch to be processed may be a highly refined starch quality (e.g., at least 90%, at least 95%, at least 97%, or at least 99.5% pure), or it may be a crude starch-containing materials comprising (e.g., milled) whole grains including non-starch fractions such as germ residues and fibers. The raw material, such as whole grains, may be reduced in particle size (e.g., by milling, in order to open up the structure and allowing for further processing). In dry milling whole kernels are milled and used. Wet milling gives a good separation of germ and meal (starch granules and protein) and is often applied at locations where the starch hydrolysate is used in the production of, for example, syrups. Both dry and wet milling are well known in the art of starch processing and may be used in a process of the instant disclosure. Methods for reducing the particle size of the starch containing material are well known to those skilled in the art.

In certain embodiments, the starch has to be thinned or "liquefied" so that it can be suitably processed. This reduction in viscosity is primarily attained by enzymatic degradation in current commercial practice. Liquefaction is generally carried out in the presence of an alpha-amylase (e.g., a bacterial alpha-amylase and/or acid fungal alpha-amylase). In certain embodiments, a phytase is also present during liquefaction. In certain other embodiments, viscosity reducing enzymes such as a xylanase and/or beta-glucanase are also present during liquefaction.

During liquefaction, the long-chained starch is degraded into branched and linear shorter units (maltodextrins) by an alpha-amylase. Liquefaction may be carried out as a three-step hot slurry process. The slurry is heated to between 60-95° C. and an alpha-amylase is added to initiate liquefaction (thinning). The slurry may be jet-cooked at between 95-140° C. (e.g., 105-125° C., for about 1-15 minutes, e.g., about 3-10 minutes, especially around 5 minutes). The slurry is then cooled to 60-95° C. and more alpha-amylase is added to obtain final hydrolysis (secondary liquefaction). The jet-cooking process is carried out at pH 4.5-6.5, typically at a pH between 5 and 6. The alpha-amylase may be added as a single dose, for example, before jet cooking. The liquefaction process is carried out at between 70-95° C., such as 80-90° C., such as around 85° C., for about 10 minutes to 5 hours, typically for 1-2 hours. The pH is between 4 and 7, such as between 4.5 and 5.5. In order to ensure optimal enzyme stability under these conditions, calcium may optionally be added (to provide 1-60 ppm free calcium ions, such as about 40 ppm free calcium ions). After such treatment, the liquefied starch will typically have a "dextrose equivalent" (DE) of 10-15. Generally, such liquefaction and liquefaction conditions are well known in the art.

Alpha-amylases for use in liquefaction can be bacterial acid stable alpha-amylases, for example an alpha-amylase is from a *Bacillus* sp. such as *Bacillus stearothermophilus* or *Bacillus licheniformis*.

Likewise, saccharification may be carried out using conditions well-known in the art with a saccharifying enzyme (e.g., a glucoamylase, a beta-amylase). For example, a complete saccharification step may last from about 24 hours to about 72 hours. Alternatively, a pre-saccharification step of approximately 40-90 minutes at a temperature between 30-65° C. (typically about 60° C.) may be used, followed by complete saccharification during fermentation in a simultaneous saccharification and fermentation (SSF) process. Saccharification is generally performed at a temperature in the range of 20-75° C. (e.g., 25-65° C. and 40-70° C., typically around 60° C.), and at a pH between about 4 and 5 (e.g., at about pH 4.5).

The saccharification and fermentation steps may be carried out either sequentially or simultaneously. In an embodiment, saccharification and fermentation are performed simultaneously (referred to as "SSF"). However, it is common to perform a pre-saccharification step for about 30 minutes to 2 hours (e.g., 30 to 90 minutes) at a temperature of 30 to 65° C., typically around 60° C. which is followed by a complete saccharification during fermentation (i.e., simultaneous saccharification and fermentation; SSF). In a simultaneous saccharification and fermentation (SSF) process, there is no holding stage for saccharification, rather, the ethanologen and enzymes are added together and the process is then carried out at a temperature of 25-40° C. (such as between 28° C. and 35° C., such as between 30° C. and 34° C., such as around 32° C.). The SSF-process may be carried out at a pH from about 3 and 7, generally from pH 4.0 to 6.5, or pH 4.5 to 5.5.

In other embodiments, ethanol is produced from starch-containing material without gelatinization (i.e., without cooking) of the starch-containing material (e.g., a "raw starch hydrolysis" process). For example, the ethanol fermentation product can be produced without liquefying the aqueous slurry containing the starch-containing material and water. Thus, in certain embodiments, the process includes saccharifying a (e.g., milled) starch-containing material (e.g., granular starch) below the initial gelatinization temperature, in the presence of saccharifying enzymes (e.g., an alpha-amylase) to produce sugars that can be fermented into ethanol by a suitable fermenting organism.

In particular embodiments, the saccharification and fermentation steps are performed simultaneously, wherein the saccharifying enzymes and fermenting organisms (e.g., a yeast strain) are added together and fermentation carried out at a temperature of 25-40° C. The SSF-process may be carried out at a pH from about 3 and 7 (e.g., pH 4.0 to 6.5, or pH 4.5 to 5.5). In certain embodiments fermentation is performed for about 6 to 120 hours.

As generally defined above, the initial gelatinization temperature means the lowest temperature at which starch gelatinization commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In certain embodiments, a temperature below the initial gelatinization temperature means that the temperature typically lies in the range between 30-75° C., preferably between 45-60° C. For example, in certain embodiments, the process is carried at a temperature from 25° C. to 40° C., such as from 28° C. to 35° C., such as from 30° C. to 34° C., preferably around 32° C.

A. Alpha-Amylases Present and/or Added in Liquefaction

Starch can be hydrolyzed into simpler carbohydrates by acids, various enzymes, or a combination thereof. For example, the primary enzymes used to hydrolyze starch into simpler carbohydrates are endo-amylases, exo-amylases, and debranching enzymes, which generally hydrolyze amylose and amylopectin. Amylose is hydrolyzed mainly by amylases, while amylopectin also requires debranching enzymes such as pullulanases (E.C. 3.2.1.41) for complete hydrolysis.

An exemplary endo-amylase is an alpha-amylase (EC 3.2.1.1), specific for a-1,4-linkages of amylose and amylopectin. Exo-amylases have the ability to hydrolyze both a-1,4-linkages and a-1,6-linkages of amylose and amylopectin. An exemplary exo-amylase is amyloglucosidase (often referred to as glucoamylase; EC 3.2.1.20). B-amylase is an enzyme that has the ability to hydrolyze the a-1,4-linkages of amylose. Debranching enzymes such as pullulanases (EC 3.2.1.41) hydrolyze a-1,6-linkages in amylopectin, wherein hydrolysis products of debranching enzymes are mainly maltotriose and maltose.

In certain embodiments, an alpha-amylase is *Bacillus stearothermophilus* alpha-amylase, or a variant thereof.

B. Glucoamylases for Use in Saccharification and/or Fermentation Processes

In certain embodiments, a carbohydrate source generating enzyme present during saccharification is a glucoamylase. Thus, in certain embodiments, a glucoamylase is present and/or added in saccharification process and/or a fermentation process. In particular embodiments, a glucoamylase is present and/or added in a simultaneous saccharification and fermentation (SSF) process.

For example, in certain embodiments, a glucoamylase present and/or added in a saccharification process and/or a fermentation process and/or in a SSF process is of fungal origin. In certain embodiments, a glucoamylase is derived from a strain of *Aspergillus* (e.g., *A. niger, A. awamori, A. oryzae*). In certain other embodiments, a glucoamylase is derived from a strain of *Trichoderma*, (e.g., *T. reesei*). In other embodiments, a glucoamylase is derived from *Talaromyces* (e.g., *T. emersonii*), *Trametes* (e.g., *T. cingulate*), and the like. In other embodiments, a glucoamylase is a variant glucoamylase derived from native glucoamylase.

Glucoamylases can be added to the saccharification and/or fermentation in an amount of 0.0001-20 AGU/g DS, such as, for example, 0.001-10 AGU/g DS, or between 0.01-5 AGU/g DS (e.g., 0.1-2 AGU/g DS or 0.1-0.5 AGU/g DS).

Commercially available compositions comprising glucoamylase are generally known to one skilled in the art. Thus, in certain other embodiments, a glucoamylase is present and/or added in saccharification and/or fermentation in combination with an alpha-amylase, described below.

C. Alpha-Amylase Present and/or Added in Saccharification and/or Fermentation

In certain embodiments, an alpha-amylase is present and/or added in a saccharification process and/or a fermentation process of the disclosure. In certain embodiments, the alpha-amylase is of a fungal origin or a bacterial origin. For example, in certain embodiments, the alpha-amylase is a fungal acid stable alpha-amylase. A fungal acid stable alpha-amylase is an alpha-amylase that has activity in the pH range of 3.0 to 7.0 and preferably in the pH range from 3.5 to 6.5, including activity at a pH of about 4.0, 4.5, 5.0, 5.5, and 6.0.

In particular embodiments, an alpha-amylase of the disclosure is derived from the genus *Aspergillus*, such as *A. terreus, A. niger, A. oryzae, A. awamori*, and *A. kawachi*. In another embodiment, an alpha-amylase of the disclosure is derived from the genus *Rhizomucor* (e.g., *R. pusillus*), or the genus *Meripilus* (e.g., *M. giganteus*).

In certain embodiments, the ratio between glucoamylase and alpha-amylase present and/or added during saccharification and/or fermentation may preferably be in the range from 500:1 to 1:1, such as from 250:1 to 1:1, such as from 100:1 to 1:1, such as from 100:2 to 100:50, such as from 100:3 to 100:70.

For example, a suitable enzyme preparation for use in saccharification includes Distillase® SSF (available from DuPont N&B), which comprises a-amylase (EC 3.2.1.1), glucoamylase (E.C. 3.2.1.3), isoamylase (EC 3.2.1.68), B-amylase (EC 3.2.1.2), pullulanase (EC 3.2.1.41) and Aspergillopepsin 1 (EC 3.4.23.18).

III. PROTEASE COMPOSITIONS AND DOSAGES

As generally set forth above, certain embodiments of the disclosure are related to the compositions and methods for the biological production of ethanol. Certain other embodiments of the disclosure are related to methods for producing ethanol comprising specific protease combinations and their use in one or more fermentation process described herein. For example, in certain embodiments, a method for producing ethanol from a starch-containing material comprises (a) liquefying a starch-containing material at a temperature above the initial gelatinization temperature of the starch-containing material in the presence of an alpha-amylase, (b) saccharifying the liquefied material obtained in step (a) using a saccharifying enzyme, and (c) fermenting the material obtained in step (b) with an ethanol production host (under suitable conditions for the production of ethanol), wherein step (b) and/or step (c) is performed in the presence of an aspartic and serine protease mixture.

In another embodiment, a method for producing ethanol from a starch-containing material comprises (a) saccharifying a starch-containing material at a temperature below the initial gelatinization temperature of the starch-containing material using a saccharifying enzyme, and (b) fermenting the material obtained in step (a) with an ethanol production host (under suitable conditions for the production of ethanol), wherein step (a) and/or step (b) is performed in the presence of an aspartic and serine protease mixture.

For example, U.S. Pat. No. 5,231,017 describes the use of an acid fungal protease during ethanol fermentation in a process generally comprising liquefying gelatinized starch with an alpha-amylase. PCT Publication No. WO2003/066826 discloses a raw starch hydrolysis process performed in the presence of a fungal glucoamylase, an alpha-amylase and a fungal protease. PCT Publication No. WO2010/008841 describes a process for producing fermentation products from gelatinized starch and/or un-gelatinized starch-containing materials by saccharifying the starch material using at least a glucoamylase and a metalloprotease (i.e., derived from *Thermoascus aurantiacus*), and fermenting using a yeast strain. PCT Publication No. WO2015/078372 describes serine protease derived from *Meripilus giganteus, Trametes versicolor* and *Dichomitus squalens* for use in a starch wet milling process. PCT Publication No. WO2016/065238 describes the use of a tripeptidyl peptidase (exo-protease) for producing an alcohol from a starch-containing feedstock. PCT Publication No. WO2019/046232 describes a process for producing ethanol from a starch-containing material by the combined use of a family M35 endo-protease and a serine protease of family S53.

More particularly, as set forth below in the Example 1 of the instant disclosure, Applicant surprisingly identified a hydrolytic synergy when combining aspartic and serine proteases in a dimethylcasein assay. For example, FIG. 1 presents the results in which a dimethylcasein assay was used to assess the proteolytic activity of each protease alone (i.e., an aspartic protease, or a serine protease) and in combination (i.e., an aspartic protease and a serine protease) to assess any synergism of the combined mixtures. As shown in FIG. 1, the results demonstrate that a combined mixture of 25 µg/ml of a serine protease (named "aorsin") and 25 µg/ml of an aspartic protease (named "A10") is more efficient in hydrolyzing dimethylcasein than either 50 µg/ml of serine protease (aorsin) alone or 50 g/ml of aspartic protease (A10) alone.

Example 2 of the disclosure further presents the results of different combinations of proteases added during fermentation of yeast cells to produce ethanol. For example, as generally described in this example, a saccharified corn liquefact was treated with either (i) a "control" treatment or (ii) "experimental" treatments. The control treatment comprised an aspartic protease (FERMGEN®) and urea (600 ppm) as the nitrogen source for the yeast cells. The experimental treatments comprised combinations of aspartic and serine proteases and urea (200 or 600 ppm) as the nitrogen source for the yeast cells. As presented in TABLE 1 of Example 2, the combination of aspartic and serine proteases outperforms the commercial Fermgen® protease with sufficient urea (600 ppm), and without sufficient urea (200 ppm).

In addition, the data presented in TABLE 2 (Example 2) demonstrate that the glycerol concentrations decrease and the ethanol concentrations increase with the experimental treatment comprising the combined of proteases (aspartic+serine) relative to the control treatment comprising the aspartic protease (FERMGEN®) in presence of sufficient urea (600 ppm). Lastly, as shown in TABLE 3 of Example 2, the experimental treatment comprising the aspartic and serine protease combination increased the ethanol concentration (14.91), with a concomitant reduction in the glycerol concentration (1.19) in the presence low urea concentrations (200 ppm), relative to the control treatment comprising the aspartic protease (FERMGEN®) in presence of high urea concentrations (600 ppm).

As shown in TABLE 4 of Example 3, the experimental treatment comprising the aspartic and serine protease combination outperforms the commercial Fermgen® (aspartic) protease in the initial fermentation rates (e.g., 16 hours, 24 hours), which aids in faster conversion of carbon to ethanol in the fermentation process.

Example 4 of the disclosure further presents and describes the results of protease combinations in a granular starch yeast fermentation process. For example, the results presented in TABLE 5 show that the experimental treatment comprising the combined proteases (aspartic+serine) outperforms the control (Fermgen®) protease treatment in the granular starch yeast fermentation process. More particularly, as shown in TABLE 15, the fermentation rates throughout the granular starch fermentation process were improved, demonstrating faster conversion of carbon to ethanol in the granular starch fermentation process.

Thus, certain embodiments of the disclosure are related to novel protease compositions for use in the production of ethanol. In certain embodiments, the novel protease compositions are used in a granular starch hydrolysis process. For example, in certain embodiments, the disclosure is directed to methods for producing ethanol from a starch-containing material comprising (a) saccharifying a starch-containing material at a temperature below the initial gelatinization temperature of the starch-containing material, using a saccharifying enzyme, and (b) fermenting the material obtained in step (a) with an ethanol production host (under suitable conditions for the production of ethanol), wherein step (a) and/or step (b) is/are performed in the presence of an aspartic and serine protease mixture.

In certain embodiments, the novel protease compositions are used in a conventional starch hydrolysis process. For example, certain embodiments are related to methods for producing ethanol from a starch-containing material comprising (a) liquefying a starch-containing material at a temperature above the initial gelatinization temperature of the starch-containing material, in the presence of an alpha-amylase, (b) saccharifying the liquefied material obtained in step (a) using a saccharifying enzyme, and (c) fermenting the material obtained in step (b) with an ethanol production host (under suitable conditions for the production of ethanol), wherein step (b) and/or step (c) is performed in the presence of an aspartic and serine protease mixture.

Thus, in certain embodiments, the disclosure is related to protease compositions comprising at least a combination of (i) an aspartic acid protease and (ii) a serine protease.

As generally set forth above in the Definitions section, an aspartic acid protease refers to any protein (enzyme) belonging to the EC 3.4.23 aspartic acid proteases. For example, aspartic proteases include, but are not limited to, Pepsin A, Pepsin B, Gastricsin, Chymosin, Cathepsin D, Cathepsin E, Nepenthesin, Renin, Aspergillopepsin I, Penicillopepsin and the like.

As generally set forth above in the Definitions section, as used herein, a "serine protease" refers to any protein (enzyme) belonging to the EC 3.4.21 serine proteases. For example, serine proteases of EC 3.4.21 include, but are not limited to Chymotrypsin, Chymotrypsin C, Trypsin, Thrombin, Aorsin, Plasmin, Kexin, Subtilisin, Granzyme B, Oryzin, Tryptase, Acrosin and the like.

In certain embodiments, a serine protease of the disclosure includes proteins (enzymes) classified as exo-type proteases (exopeptidases). Thus, in certain embodiments, a serine protease of the disclosure includes enzymes classified as exo-type proteases (exopeptidases), such as EC 3.4.14.

In certain other embodiments, a serine protease of the disclosure is limited to endo-type protease (endopeptidase). For example, in particular embodiments, a serine protease of the disclosure excludes proteins (enzymes) classified as an exo-type protease (exopeptidases). Thus, in other embodiments, a serine protease of the disclosure excludes any protein (enzyme) belonging to the EC 3.4.14 group (e.g., excluding exopeptidases such as dipeptidyl-peptidase I, dipeptidyl-peptidase II, tripeptidyl-peptidase I, tripeptidyl-peptidase II, and the like).

In certain embodiments, an aspartic acid protease of the disclosure comprises about 50% to 100% sequence identity to the aspartic acid protease of SEQ ID NO: 2. For example, in certain embodiments, an aspartic acid protease of the disclosure comprises about 55%, about 60%, about 65%, about 70%, about 75%, about 80%, about 85%, about 90%, or about 99% sequence identity to the aspartic acid protease of SEQ ID NO: 2.

In other embodiments, a serine protease of the disclosure comprises about 50% to 100% sequence identity to the serine protease of SEQ ID NO: 4. For example, in certain embodiments, a serine protease of the disclosure comprises about 55%, about 60%, about 65%, about 70%, about 75%, about 80%, about 85%, about 90%, or about 99% sequence identity to the serine protease of SEQ ID NO: 4.

In particular embodiments, the novel aspartic and serine protease compositions of the disclosure are admixed with a starch-containing material. In certain embodiments, the aspartic and serine protease compositions are admixed with a starch-containing material after liquefying the starch-containing material. In another embodiment, the aspartic and serine protease compositions are admixed with a starch-containing material after liquefying and saccharifying the starch-containing material. In certain embodiments, the aspartic and serine protease compositions are used in granular starch hydrolysis process. In particular embodiments, the aspartic and serine protease compositions are admixed with a granular starch composition and used in a simultaneous saccharification and fermentation (SSF) process.

As described herein, the aspartic and serine protease compositions (mixtures) and methods of the instant disclosure are particularly useful for enhancing the rates of ethanol production in a fermentation process thereof, and/or for increasing ethanol yields in a fermentation process thereof, and/or for reducing glycerol yields in a fermentation process thereof, and/or for lowering supplemental nitrogen requirements (e.g., urea) in a fermentation process thereof and the like.

Thus, the aspartic and serine protease mixtures described herein for use in the methods of the present disclosure may be dosed in any suitable amount. In certain embodiments, an aspartic and serine protease composition (mixture) may be dosed in an amount of about 5 mg to 3 g of aspartic protease and about 5 mg to 3 g of serine protease per kg of starch-containing material (feedstock). In other embodiments, the aspartic and serine protease composition (mixture) may be dosed in an amount of about 25 mg to 1000 mg of aspartic protease and 25 mg to 1000 mg of serine protease per kg of starch-containing material (feedstock). Thus, in certain other embodiments, the aspartic and serine protease composition (mixture) may be dosed in an amount of about 0.01 mg to 100 mg; 0.5 mg to 100 mg; 1 mg to 50 mg; 5 mg to 100 mg; 5 mg to 20 mg, 10 mg to 100 mg; 0.05 mg to 50 mg; or 0.10 mg to 10 mg of enzyme per kg of feedstock.

For example, as described in below in Example 1 (e.g., see, FIG. 1), the combination of the aspartic (25 µg/ml) and serine (25 µg/ml) proteases (i.e., equivalent amounts) demonstrates synergy in hydrolyzing substrate (i.e., dimethylcasein) relative to either the aspartic (A10) protease alone (50 µg/ml), or the serine (aorsin) protease alone (50 µg/ml). Thus, in certain embodiments, an aspartic and serine protease composition (mixture) may be dosed in an amount where the aspartic protease and serine protease are approximately equivalent. For example, an equivalent amount of aspartic and serine protease may be based on equivalent aspartic and serine protease concentrations, equivalent aspartic and serine protease activities, and the like. The exact amount will generally depend on the particular type of starch-containing material employed and on the specific protease activity per mg of protein.

In other embodiments, the aspartic and serine protease composition may be dosed in an amount based on grams of dry solids present in a feedstock.

IV. FERMENTING STARCH-CONTAINING MATERIALS TO PRODUCE ETHANOL

As described herein, the fermentation conditions are generally determined based on the type of plant (starch-containing) material used, the available fermentable sugars and/or the fermenting organism(s) used in the fermentation process. One skilled in the art can readily determine suitable fermentation conditions. The fermentation may be carried out at conventionally used conditions. Preferred fermentation processes are anaerobic processes.

For example, fermentations may be carried out at temperatures as high as 75° C. (e.g., between 40-70° C., such as between 50-60° C.). However, bacteria with a significantly lower temperature optimum down to around room temperature (around 20° C.) are also known. Examples of suitable fermenting organisms can be found in the Ethanol Production Hosts section below.

For ethanol production using yeast, the fermentation may go on for 24 to 96 hours, in particular for 35 to 60 hours. In certain embodiments, the fermentation is carried out at a temperature between 20° C. to 40° C., preferably 26° C. to 34° C., in particular around 32° C. The fermentation may include, in addition to a fermenting microorganisms (e.g., yeast), nutrients, and additional enzymes, including phytases. The use of yeast in fermentation is well known in the art.

Fermentation is typically carried out at a pH in the range between 3 and 7 (e.g., pH 3.5 to 6, or pH 4 to 5. Fermentations are typically ongoing for 6-96 hours. The fermentation processes of the disclosure may be performed as a batch process or as a continuous process. Fermentations may be conducted in an ultrafiltration system wherein the retentate is held under recirculation in the presence of solids, water, and the fermenting organism, and wherein the permeate is the desired fermentation product containing liquid. Likewise, contemplated are methods/processes conducted in continuous membrane reactors with ultrafiltration membranes and where the retentate is held under recirculation in presence of solids, water, and the fermenting organism(s) and where the permeate is the fermentation product containing liquid. After fermentation the fermenting organism may be separated from the fermented slurry and recycled.

V. ETHANOL PRODUCTION HOSTS

In certain embodiments, an ethanol production host may be a bacterium from one or more genus selected from the group consisting of *Zymomonas, Arthrobacter, Bacillus, Clostridium, Erwinia, Escherichia, Klebsiella, Lactobacillus, Pseudomonas, Streptomyces* and *Thermoanaerobacter*. In one particular embodiment the bacterium is *Zymomonas mobilis* or *Escherichia coli*.

In other embodiments an ethanol production host may be a fungus. The fungus for use in accordance with the present invention may be any ascomycetous fungus (e.g., an Ascomycete).

In certain embodiments, an ethanol production host is a yeast. Suitably the yeast may be selected from the group consisting of *Saccharomyces, Kluyveromyces, Zygosaccharomyces, Issatchenkia, Kazachstania* and *Torulaspora*. In other embodiments, the yeast may be one or more selected from the group consisting of *Saccharomyces cerevisiae, Saccharomyces bayanus, Saccharomyces carlsbergensis, Saccharomyces kudriavtsevii, Saccharomyces kudriavzevii* and *Saccharomyces pastorianus*. In another embodiment, the ethanol production host is a *Saccharomyces cerevisiae* var. *diastaticus* yeast.

In certain embodiments, an ethanol production host (e.g., active yeast) is added before, during, or after adding an aspartic and serine protease composition to a starch-containing material (feedstock).

For example, *Saccharomyces cerevisiae* is commonly used in the commercial production of ethanol, wherein *S. cerevisiae* is proficient in fermenting glucose to ethanol (e.g., often to concentrations greater than 20% w/v). However, *S. cerevisiae*'s ability to generate a nitrogen source is limited, which either slows down fermentation, or requires the addition of an exogenous nitrogen sources such as urea. More particularly, as generally set forth above and described in the Examples section herewith, the novel aspartic and serine protease mixtures (combinations) of the disclosure improve the ability of the ethanol production host to ferment starch-containing materials in such starch to ethanol fermentation processes described. For example, it was observed herein that the addition an aspartic and serine protease mixture (combination) of the disclosure increases the rate of fermentation by supplying free amino acids via hydrolysis of protein found in the starch-containing material (e.g., corn). Thus, the use of such aspartic and serine protease mixtures (combinations) of the disclosure advantageously reduce (decrease) the amount of exogenous nitrogen (e.g., urea) that needs to be added during fermentation, thereby reducing the overall cost of such starch to ethanol fermentation processes.

In certain embodiments, an improvement in the ethanol production host's ability to ferment in the presence of an aspartic and serine protease combination may be measured by an increase in the amount of glucose consumed during fermentation by the ethanol production host when compared (relative) to the level of glucose consumed during fermentation by the ethanol production host in the presence of an aspartic protease and/or when compared (relative) to the level of glucose consumed during fermentation by the ethanol production host in the presence of a serine protease.

Modified Ethanol Production Hosts

In certain embodiments, the disclosure is related methods for producing ethanol from a starch-containing material comprising fermenting a starch-containing material with an ethanol production host (under suitable conditions for the production of ethanol), wherein the ethanol production host expresses and secretes a heterologous aspartic protease and a heterologous serine protease, and recovering the ethanol produced. In other embodiments, the disclosure is related to methods for producing ethanol from a starch-containing material comprising fermenting a starch-containing material with at least two ethanol production hosts under suitable conditions for the production of ethanol, wherein a first ethanol production host expresses and secretes a heterologous aspartic protease and a second ethanol production host expresses and secretes a heterologous serine protease, and recovering the ethanol produced.

Thus, in certain embodiments, heterologous nucleic acid molecules (i.e., nucleic acid sequences) are introduced into a host cell of the disclosure, which heterologous nucleic acid molecules may be codon-optimized with respect to the intended recipient host cell. Methods for introducing polynucleotides (e.g., expression cassettes) into microbial host cells (strains) are well known to the skilled artisan.

More particularly, in certain embodiments, a heterologous nucleic acid sequence of the disclosure encodes an aspartic acid protease. In other embodiments, a heterologous nucleic acid sequence of the disclosure encodes a serine acid protease. In certain embodiments, a heterologous nucleic acid sequence encoding an aspartic protease, or heterologous nucleic acid sequence encoding a serine protease, comprises a gene, or an open reading frame (ORF) thereof encoding the aspartic or serine protease operably linked to an upstream (5') promoter sequence, and optionally operably linked to a downstream (3') terminator sequence.

VI. COMBINATION WITH OTHER COMPONENTS

The proteases of the disclosure may be formulated in any manner known in the art. In certain embodiments, the aspartic protease and/or the serine protease for use in the present disclosure may be formulated as a liquid, a dry powder or a granule. Thus, in certain embodiments, the aspartic protease and/or the serine protease are formulated as a liquid formulation. In another embodiment, the aspartic protease and/or the serine protease are formulated as a dry powder.

In some embodiments, further ingredients may be admixed with the aspartic and/or serine proteases, such as salts such as $Na_2SO_4$, maltodextrin, limestone (calcium carbonate), cyclodextrin, wheat or a wheat component, starch, Talc, PVA, polyols such as sorbitol and glycerol, benzoate, sorbiate, sugars such as sucrose and glucose, propylene glycol, 1,3-propane diol, parabens, sodium chloride, citrate, acetate, sodium acetate, phosphate, calcium, metabisulfite, formate or mixtures thereof, and the like.

In one embodiment, the salt may be selected from the group consisting of: $Na_2SO_4$, $NaH_2PO_4$, $Na_2HPO_4$, $Na_3PO_4$, $(NH_4)H_2PO_4$, $K_2HPO_4$, $KH_2PO_4$, $K_2SO_4$, $KHSO_4$, $ZnSO_4$, $MgSO_4$, $CuSO_4$, $Mg(NO_3)_2$, $(NH_4)_2SO_4$, sodium borate, magnesium acetate, sodium citrate or combinations thereof.

A dry powder or granules may be prepared by means known to those skilled in the art, such as, in top-spray fluid bed coater, drum granulation (e.g., high sheer granulation), extrusion, pan coating, and the like.

Suitably, the aspartic protease and/or the serine protease may be dried with an ethanol production host. In certain embodiments, the aspartic protease and/or the serine protease may be coated, for example encapsulated. For example, such coatings can protect the aspartic protease and/or the serine protease from heat inactivation and may be considered a thermo-protectant.

In other embodiments, the aspartic protease and/or the serine protease may be diluted using a diluent, such as starch powder, lime stone and the like In another embodiment, the aspartic protease and/or the serine protease may be formulated by applying (e.g., spraying) the enzyme(s) onto a carrier substrate, such as ground wheat for example.

In certain other embodiments, the methods and/or compositions of the disclosure may further comprise one or more enzymes comprising cellulase activity, hemicellulase activity, and combinations thereof. Suitably the one or more enzymes comprising cellulase activity and/or hemicellulase activity, are selected from the group consisting endoglucanases (EC 3.2.1.4); cellobiohydrolases (EC 3.2.1.91), B-glucosidases (EC 3.2.1.21), cellulases (EC 3.2.1.74), lichenases (EC 3.1.1.73), lipases (EC 3.1.1.3), lipid acyltransferases (generally classified as EC 2.3.1.x), phospholipases (EC 3.1.1.4, EC 3.1.1.32 or EC 3.1.1.5), phytases (e.g., 6-phytase (EC 3.1.3.26) or a 3-phytase (EC 3.1.3.8), acid phosphatase, amylases, alpha-amylases (EC 3.2.1.1), xylanases (e.g., endo-1,4-B-d-xylanase (E.C. 3.2.1.8) or 1,4 B-xylosidase (EC 3.2.1.37) or EC 3.2.1.32, EC 3.1.1.72, EC 3.1.1.73), glucoamylases (EC 3.2.1.3), pullulanases, hemicellulases, a keratinase (EC 3.4.x.x), debranching enzymes, cutinases, esterases and/or mannanases (e.g., a B-mannanase (EC 3.2.1.78)) transferases, glucosidases, arabinofuranosidase, and a phytase (e.g., a 6-phytase (EC 3.1.3.26) or a 3-phytase (EC 3.1.3.8)).

VII. EXEMPLARY EMBODIMENTS

Non-limiting embodiments of compositions and methods disclosed herein are as follows:

1. A method for producing ethanol from a starch-containing material comprising (a) liquefying a starch-containing material at a temperature above the initial gelatinization temperature of the starch-containing material in the presence of an alpha-amylase, (b) saccharifying the liquefied material obtained in step (a) using a saccharifying enzyme, and (c) fermenting the material obtained in step (b) with an ethanol production host under suitable conditions for the production of ethanol, wherein step (b) and/or step (c) is performed in the presence of an aspartic and serine protease mixture.

2. A method for producing ethanol from a starch-containing material comprising (a) saccharifying a starch-containing material at a temperature below the initial gelatinization temperature of the starch-containing material using a saccharifying enzyme, and (b) fermenting the material obtained is step (a) with an ethanol production host under suitable conditions for the production of ethanol, wherein step (a) and/or step (b) is performed in the presence of an aspartic and serine protease mixture.

3. The method of embodiment 1 or embodiment 2, wherein saccharification and fermentation are performed simultaneously.

4. The method of embodiment 1 or embodiment 2, further comprising recovering the ethanol produced.

5. The method of embodiment 1, wherein the alpha-amylase in step (a) is a thermostable alpha-amylase.

6. The method of embodiment 1 or embodiment 2, wherein an alpha-amylase is present or added during saccharification and/or fermentation.

7. The method of embodiment 1 or embodiment 2, wherein the saccharifying enzyme is selected from the group consisting of a glucoamylase, an alpha-glucosidase, a maltogenic amylase, a pullulanase and a beta-amylase.

8. The method of embodiment 1 or embodiment 2, wherein the serine protease excludes enzymes designated EC 3.4.14.

9. The method of embodiment 1 or embodiment 2, wherein the serine protease excludes enzymes designated EC 3.4.16.

10. The method of embodiment 1 or embodiment 2, wherein the aspartic and serine protease mixture comprises about 5% (w/w) aspartic protease and about 95% serine protease (w/w) on a total protease basis, or comprises 10% (w/w) aspartic protease and 90% serine protease (w/w) on a total protease basis, or comprises 20% (w/w) aspartic protease and 80% serine protease (w/w) on a total protease basis, or comprises 30% (w/w) aspartic protease and 70% serine protease (w/w) on a total protease basis, or comprises 40% (w/w) aspartic protease and 60% serine protease (w/w) on a total protease basis, or comprises 50% (w/w) aspartic protease and 50% serine protease (w/w) on a total protease basis, or comprises 60% (w/w) aspartic protease and 40% serine protease (w/w) on a total protease basis, or comprises 70% (w/w) aspartic protease and 30% serine protease (w/w) on a total protease basis, or comprises 80% (w/w) aspartic protease and 20% serine protease (w/w) on a total protease basis, or comprises 90% (w/w) aspartic protease and 10% serine protease (w/w) on a total protease basis, or comprises about 95% (w/w) aspartic protease and 5% serine protease (w/w) on a total protease basis 11. The method of embodiment 1, wherein the amount of ethanol produced is increased relative to amount of ethanol produced using the same method except for wherein step (b) and/or step (c) is performed in the presence of aspartic protease, or a serine protease, but not a mixture thereof.

12. The method of embodiment 2, wherein the amount of ethanol produced is increased relative to amount of ethanol produced using the same method except for wherein step (a) and/or step (b) is performed in the presence of aspartic protease, or a serine protease, but not a mixture thereof.

13. The method of embodiment 1, wherein the rate of ethanol production is increased relative to the rate of ethanol production using the same method except for wherein step (b) and/or step (c) is performed in the presence of aspartic protease, or a serine protease, but not a mixture thereof.

14. The method of embodiment 2, wherein the rate of ethanol production is increased relative to the rate of ethanol production using the same method except for wherein step (a) and/or step (b) is performed in the presence of aspartic protease, or a serine protease, but not a mixture thereof 15. The method of embodiment 1, wherein the amount of glycerol produced is reduced relative to the amount of glycerol produced using the same method except for wherein step (b) and/or step (c) is performed in the presence of aspartic protease, or a serine protease, but not a mixture thereof.

16. The method of embodiment 2, wherein the amount of glycerol produced is reduced relative to the amount of glycerol produced using the same method except for wherein step (a) and/or step (b) is performed in the presence of aspartic protease, or a serine protease, but not a mixture thereof.

17. The method of embodiment 1, wherein the ethanol production host requires a reduced amount supplemented nitrogen relative to the same ethanol production host fermented using the same method except for wherein step (b) and/or step (c) is performed in the presence of aspartic protease, or a serine protease, but not a mixture thereof.

18. The method of embodiment 2, wherein the ethanol production host requires a reduced amount supplemented nitrogen relative to the same ethanol production host fermented using the same method except for wherein step (a) and/or step (b) is performed in the presence of aspartic protease, or a serine protease, but not a mixture thereof.

19. The method of embodiment 1 or embodiment 2, wherein starch-containing material is derived from barley, beans, cassava, cereals, corn, milo, peas, potatoes, rice, rye, sago, sorghum, sweet potatoes, tapioca, wheat, whole grains, or any combination thereof.

20. The method of embodiment 1 or embodiment 2, wherein the ethanol production host is a yeast cell.

21. The method of embodiment 1 or embodiment 2, wherein the aspartic protease comprises about 60% sequence identity to the aspartic protease of SEQ ID NO: 2 or SEQ ID NO: 6 and the serine protease comprises about 60% sequence identity to the serine protease of SEQ ID NO: 4.

22. A method for producing ethanol from a starch-containing material comprising fermenting a starch-containing material with an ethanol production host under suitable conditions for the production of ethanol, wherein the ethanol production host expresses and secretes a heterologous aspartic protease and a heterologous serine protease, and recovering the ethanol produced.

23. A method for producing ethanol from a starch-containing material comprising fermenting a starch-containing material with at least two ethanol production hosts under suitable conditions for the production of ethanol, wherein a first ethanol production host expresses and secretes a heterologous aspartic protease and a second ethanol production host expresses and secretes a heterologous serine protease, and recovering the ethanol produced.

24. The method of embodiment 22 or embodiment 23, wherein starch-containing material is derived from barley, beans, cassava, cereals, corn, milo, peas, potatoes, rice, rye, sago, sorghum, sweet potatoes, tapioca, wheat, whole grains, or any combination thereof.

25. The method of embodiment 22 or embodiment 23, wherein the starch-containing material has been liquefied and saccharified.

26. The method of embodiment 22 or embodiment 23, wherein the starch-containing material is a raw starch composition 27. The method of embodiment 22 or embodiment 23, wherein the ethanol production host is a yeast cell.

28. The method of embodiment 22, wherein the ethanol production host comprises an introduced expression cassette encoding the heterologous aspartic protease and an introduced expression cassette encoding the heterologous serine protease.

29. The method of embodiment 23, wherein the first ethanol production host comprises an introduced expression cassette encoding the heterologous aspartic protease and the second ethanol production host comprises an introduced expression cassette encoding the heterologous serine protease.

30. The method of embodiment 22 or embodiment 23, wherein the serine protease excludes enzymes designated EC 3.4.14.

31. The method of embodiment 22 or embodiment 23, wherein the serine protease excludes enzymes designated EC 3.4.16.

32. A protease composition comprising a mixture of an aspartic protease and a serine protease.

33. The protease composition of embodiment 32, for use in producing ethanol from a starch-containing material.

34. The protease composition of embodiment 32, wherein the aspartic protease comprises about 60% sequence identity to the aspartic protease of SEQ ID NO: 2 or SEQ ID NO: 6 and the serine protease comprises about 60% sequence identity to the serine protease of SEQ ID NO: 4.

35. The protease composition of embodiment 32, wherein the serine protease excludes enzymes designated EC 3.4.14.

36. The protease composition of embodiment 32 wherein the serine protease excludes enzymes designated EC 3.4.16.

37. The protease composition of embodiment 32, admixed with a starch-containing material.

38. The protease composition of embodiment 32, admixed with a starch-containing material after liquefying the starch-containing material.

39. The protease composition of embodiment 32, admixed with a granular starch composition obtained from a starch-containing material.

40. The protease composition of embodiment 32, admixed with a starch-containing material in a simultaneous saccharification and fermentation (SSF) process.

41. The protease composition of embodiment 30, wherein the aspartic and serine protease mixture comprises about 5% (w/w) aspartic protease and about 95% serine protease (w/w) on a total protease basis, or comprises 10% (w/w) aspartic protease and 90% serine protease (w/w) on a total protease basis, or comprises 20% (w/w) aspartic protease and 80% serine protease (w/w) on a total protease basis, or comprises 30% (w/w) aspartic protease and 70% serine protease (w/w) on a total protease basis, or comprises 40% (w/w) aspartic protease and 60% serine protease (w/w) on a total protease basis, or comprises 50% (w/w) aspartic protease and 50% serine protease (w/w) on a total protease basis, or comprises 60% (w/w) aspartic protease and 40% serine protease (w/w) on a total protease basis, or comprises 70% (w/w) aspartic protease and 30% serine protease (w/w) on a total protease basis, or comprises 80% (w/w) aspartic protease and 20% serine protease (w/w) on a total protease basis, or comprises 90% (w/w) aspartic protease and 10% serine protease (w/w) on a total protease basis, or comprises about 95% (w/w) aspartic protease and 5% serine protease (w/w) on a total protease basis 42. The protease composition of embodiment 32, wherein starch-containing material is derived from barley, beans, cassava, cereals, corn, milo, peas, potatoes, rice, rye, sago, sorghum, sweet potatoes, tapioca, wheat, whole grains, or any combination thereof.

EXAMPLES

Certain aspects of the present disclosure may be further understood in light of the following examples, which should not be construed as limiting. Modifications to materials and methods will be apparent to those skilled in the art.

Example 1

Hydrolytic Synergy Between Aspartic and Serine Proteases

An aspartic protease from *T. reesei* named "A10" protease was produced by expressing a cloned *T. reesei* gene (SEQ ID NO: 1) in a *T. reesei* strain under expressional control of a strong cbhI promoter. The methods for over-expression of genes in *T. reesei* under control of the cbhI promoter are well known in the art and *T. reesei* strains suitable for such expression are available from public strain collections (e.g. RUT-C30 or RL-P37). The recombinant A10 protease (SEQ ID NO: 2) is expressed in high yield relative to background protease activity in *T. reesei*. For example, proteolytic activity of the parental *T. reesei* strain without the recombinant cassette for expression of the A10 protease is undetectable by the methods described herein and can therefore be considered negligible. Likewise, a serine protease from *A. niger* named "aorsin" protease (which is active at acidic pH values) was produced by expressing a cloned *A. niger* gene (SEQ ID NO: 3) in a *T. reesei* strain under expressional control of a strong cbhI promoter, using the same methods as described for the A10 protease. Similar to the A10 protease, the aorsin protease (SEQ ID NO: 4) was expressed at high levels, such that any proteolytic activity in the culture supernatant except for the aorsin (activity) can be considered negligible. Culture supernatants of the A10 expressing *T. reesei* strain and the aorsin expressing *T. reesei* strain were concentrated by ultrafiltration and used without further purification.

As shown in FIG. 1, dimethylcasein was used to assay the proteolytic activity of each protease alone (aspartic or serine) and in combination (aspartic+serine) to assess any synergism of the combined mixtures. Arguably, this is the most universal protease assay, as it measures total amount of free N-termini generated in a proteolytic reaction.

The assay was performed in 0.2 M sodium acetate buffer, pH 4.5 containing 5 mg/ml dimethylcasein (Sigma Aldrich C9801). The reaction was initiated by addition of 50 µg/ml of protease and run at 37° C. In samples where a mixture of two (2) proteases were used, twenty-five (25) µg/ml of each protease (25 µg/ml aspartic+25 µg/ml serine) was added. Twenty (20) µl aliquots were taken at indicated time intervals (0-120 minutes) and frozen on dry ice until the end of run. The aliquots were mixed with 200 µl of 0.05% trinitrobenzene sulfonic acid in 0.2 M sodium borate buffer, pH 8.6. Reagents were mixed well and incubated at 37° C. for 15 minutes. Twenty (20) µl aliquots of these reaction mixtures were taken into a clear MTP plate and diluted with 100 µl of water. The optical density ($OD_{410\ nm}$) was measured using a microtiter plate reader. The results are presented in FIG. 1, which clearly indicate that a mixture of 25 µg/ml of aorsin (serine) protease and 25 µg/ml of A10 (aspartic) protease is more efficient in hydrolyzing dimethylcasein than either 50 µg/ml of aorsin (serine) protease alone or 50 µg/ml of A10 (aspartic) protease alone.

Example 2

The Influence of Proteases During Yeast Fermentation

The instant example presents the results of different combinations of proteases added during fermentation of yeast cells to produce ethanol. Thus, the data presented herein generally relates to yeast fermentation rates, ethanol concentrations and/or glycerol concentrations thereof. More particularly, a novel combination of serine and aspartic proteases was compared against a commercial protease (DuPont; FERMGEN®).

For example, the corn liquefact from a commercial dry grind ethanol plant was collected and frozen to be used for this experiment. The frozen liquefact was thawed at 65° C. for three (3) hours to pasteurize. The liquefact was cooled to room temperature, the pH was adjusted to pH 4.8 with ammonium hydroxide and sulfuric acid. Saccharifying enzymes were added equivalent to 0.325 GAUs/g ds with constant mixing. The liquefact was aliquoted into 125 mL Erlenmeyer flasks in 100 g weights. For the control treatment, FERMGEN® protease and urea (600 ppm) as nitrogen source for the yeast was added. For the experimental protease treatment, the urea was added at 200 ppm and 600 ppm levels with combinations of aspartic and serine proteases. Active dry yeast was added at 0.01% w/w dosage to all of the flasks and the rubber stoppers with small holes were plugged on top the flasks.

Initial weights of all the flasks were noted and the flasks were placed in air heated incubators at 32° C. at 200 rpm for sixty-two (62) hours. Regular weights of the flasks were noted (i.e., at 16, 24, 40, 48 and 62 hours of incubation) to follow the weight loss as $CO_2$ produced in parallel with ethanol produced from the glucose. Samples were taken at the end of fermentation at sixty-two (62) hours to be processed and prepared for the HPLC for measuring ethanol, glycerol, sugar and organic acid concentrations.

The results are presented below in TABLES 1-3 and show that the addition of novel combinations of aspartic and serine proteases improves fermentation rates, final ethanol concentrations and reduces the glycerol by-product, which improves the carbon conversion fermentation efficiency of the yeast ethanol production.

TABLE 1

| Weight Loss (g) Measurement Over the SSF Incubation with and without Sufficient Urea | | | | | |
|---|---|---|---|---|---|
| | Hours | | | | |
| Treatments | 16 | 24 | 40 | 48 | 62 |
| 600 ppm Urea + Fermgen ® | 5.55 | 8.35 | 11.29 | 12.03 | 12.42 |
| 200 ppm Urea + Fermgen ® | 5.01 | 7.49 | 10.26 | 11.05 | 11.87 |

TABLE 1-continued

| Weight Loss (g) Measurement Over the SSF Incubation with and without Sufficient Urea | | | | | |
|---|---|---|---|---|---|
| | Hours | | | | |
| Treatments | 16 | 24 | 40 | 48 | 62 |
| 600 ppm Urea + aspartic protease + serine protease | 6.01 | 8.94 | 11.93 | 12.35 | 12.55 |
| 200 ppm Urea + aspartic protease + serine protease | 5.77 | 8.61 | 11.64 | 12.28 | 12.60 |
| 200 ppm Urea + aspartic protease | 5.79 | 8.60 | 11.54 | 12.13 | 12.43 |
| 200 ppm Urea + serine protease | 5.54 | 8.31 | 11.29 | 12.01 | 12.45 |

As shown above in TABLE 1, the novel combination of aspartic and serine proteases outperforms the commercial Fermgen® protease with (600 ppm) and without (200 ppm) sufficient urea.

TABLE 2

| Ethanol and Glycerol Concentrations (% Weight/Volume) in Presence of High Urea Concentrations (600 ppm) | | |
|---|---|---|
| Treatments | Glycerol % (w/v) | Ethanol % (w/v) |
| 600 ppm Urea + Fermgen ® | 1.26 | 14.76 |
| 600 ppm Urea + aspartic protease + serine protease | 1.17 | 14.84 |

As presented above in TABLE 2, the glycerol concentration decreases and the ethanol concentration increases with the addition of the novel combination of proteases, relative to the control protease FERMGEN® in presence of sufficient urea (600 ppm).

TABLE 3

| Ethanol and Glycerol Concentrations in Presence of Low Urea Concentrations (200 ppm) at 62 hr | | |
|---|---|---|
| Treatments | Glycerol % w/v | Ethanol % w/v |
| 600 ppm Urea + Fermgen ® | 1.26 | 14.76 |
| 200 ppm Urea + Fermgen ® | 1.32 | 13.75 |
| 200 ppm Urea + aspartic protease | 1.20 | 14.79 |
| 200 ppm Urea + serine protease | 1.23 | 14.82 |
| 200 ppm Urea + aspartic protease + serine protease | 1.19 | 14.91 |

As presented above in TABLE 3, addition of the aspartic and serine protease combination increased the ethanol concentration (14.91) with a concomitant reduction in the glycerol concentration (1.19) in the presence low urea concentrations (200 ppm) relative to (vis-a-vis) the control protease (FERMGEN®) in presence of high urea concentrations (600 ppm).

Example 3

The Influence of Proteases During Yeast Fermentation

The instant example presents the results of different combinations of aspartic and serine (i.e., sedolisin) proteases added during fermentation of yeast cells to produce ethanol. Thus, the data presented herein generally relates to yeast fermentation rates. More particularly, a novel combination of serine and aspartic proteases was compared against a commercial aspartic protease (DuPont; FERMGEN®).

For example, the corn liquefact from a commercial dry grind ethanol plant was collected and frozen to be used for this experiment. The frozen liquefact was thawed at 65° C. for three (3) hours to pasteurize. The liquefact was cooled to room temperature, the pH was adjusted to pH 4.8 with ammonium hydroxide and sulfuric acid. Saccharifying enzymes were added equivalent to 0.325 GAUs/g ds with constant mixing. The liquefact was aliquoted into 125 mL Erlenmeyer flasks in 100 g weights. For the control treatment, FERMGEN® protease and urea (200 ppm) as nitrogen source for the yeast was added. For the experimental protease treatment, the urea was added at 200 ppm levels with combinations of aspartic and serine (sedolisin) protease. Active dry yeast was added at 0.01% w/w dosage to all of the flasks and the rubber stoppers with small holes were plugged on top the flasks.

Initial weights of all the flasks were noted and the flasks were placed in air heated incubators at 32° C. at 200 rpm for sixty-two (62) hours. Regular weights of the flasks were noted (i.e., at 16, 24, 40, 48 and 62 hours of incubation) to follow the weight loss as $CO_2$ produced in parallel with ethanol produced from the glucose.

The results are presented below in TABLE 4, which show that the addition of novel combinations of aspartic and serine improves fermentation rates at 16 hours and 24 hours, which improves the carbon conversion fermentation efficiency and time taken to finish the fermentation of the yeast ethanol production.

TABLE 4

| Weight Loss (g) Measurement Over the SSF Incubation | | | | | |
|---|---|---|---|---|---|
| | Hours | | | | |
| Treatments | 16 | 24 | 40 | 48 | 62 |
| 200 ppm Urea + FERMGEN ® | 5.27 | 7.07 | 10.29 | 10.84 | 11.71 |
| 200 ppm Urea + aspartic protease | 6.09 | 8.11 | 11.60 | 12.06 | 12.51 |
| 200 ppm Urea + aspartic protease + serine protease | 6.37 | 8.31 | 11.61 | 12.05 | 12.53 |

Thus, as presented above in TABLE 4, the novel combination of aspartic and serine (sedolisin) outperforms the commercial Fermgen® protease in the initial fermentation rates, which aids in faster conversion of carbon to ethanol in the fermentation process.

Example 4

The Influence of Proteases During Granular Starch Yeast Fermentation

The instant example presents the results from a granular starch yeast fermentation of different combinations of aspartic and serine proteases added during fermentation to produce ethanol. Thus, the data presented herein generally relates to yeast fermentation rates. More particularly, a novel combination of serine and aspartic proteases was compared against a commercial aspartic protease (DuPont; FERMGEN®).

For example, ground corn flour was collected for this experiment. The ground corn flour was mixed with filtered tap water and the pH was adjusted to pH 4.8 with ammonium hydroxide and sulfuric acid. Saccharifying enzymes were added equivalent to 1.0 GAUs/g ds with constant mixing. The ground corn slurry was aliquoted into 125 mL Erlenmeyer flasks in 100 g weights. For the control treatment, FERMGEN® protease and urea (600 ppm) as nitrogen source for the yeast was added. For the experimental protease treatment, the urea was added at 600 ppm levels with combinations of aspartic and serine proteases. Active dry yeast was added at 0.01% w/w dosage to all of the flasks and the rubber stoppers with small holes were plugged on top the flasks.

Initial weights of all the flasks were noted and the flasks were placed in air heated incubators at 32° C. at 200 rpm for sixty-two (62) hours. Regular weights of the flasks were noted (i.e., at 17, 24, 41, 62 and 86 hours of incubation) to follow the weight loss as $CO_2$ produced in parallel with ethanol produced from the glucose.

The results are presented below in TABLE 5 and show that the addition of novel combinations of aspartic and serine (sedolisin) proteases improves fermentation rates throughout the granular starch fermentation which improves the carbon conversion fermentation efficiency and time taken to finish the fermentation of the yeast ethanol production.

TABLE 5

| Weight Loss (g) Measurement Over the Granular Starch Fermentation | | | | | |
|---|---|---|---|---|---|
| | Hours | | | | |
| Treatments | 17 | 24 | 41 | 62 | 86 |
| FERMGEN ® | 4.47 | 5.56 | 8.71 | 11.20 | 12.16 |
| Aspartic protease + Serine protease | 4.58 | 5.69 | 8.92 | 11.37 | 12.29 |

As shown above in TABLE 5, the novel combination of aspartic and serine protease outperforms the commercial Fermgen® protease in the fermentation rates throughout the incubation which helps in faster conversion of carbon to ethanol in the granular starch fermentation process.

The invention claimed is:

1. A method for producing ethanol from a starch-containing material comprising:
   (a) liquefying a starch-containing material at a temperature above the initial gelatinization temperature of the starch-containing material in the presence of an alpha-amylase,
   (b) saccharifying the liquefied material obtained in step (a) using a saccharifying enzyme, and
   (c) fermenting the material obtained in step (b) with an ethanol production host under suitable conditions for the production of ethanol,
   wherein step (b) and/or step (c) is performed in the presence of an aspartic and serine protease mixture, and wherein the aspartic protease comprises SEQ ID NO: 2 and the serine protease comprises SEQ ID NO: 4.

2. A method for producing ethanol from a starch-containing material comprising:
   (a) saccharifying a starch-containing material at a temperature below an initial gelatinization temperature of the starch-containing material using a saccharifying enzyme, and
   (b) fermenting the material obtained is step (a) with an ethanol production host under suitable conditions for the production of ethanol,
   wherein step (a) and/or step (b) is performed in the presence of an aspartic and serine protease mixture,
   wherein the aspartic protease comprises SEQ ID NO: 2 and the serine protease comprises SEQ ID NO: 4.

3. The method of claim 1, wherein saccharification and fermentation are performed simultaneously.

4. The method of claim 2, wherein saccharification and fermentation are performed simultaneously.

\* \* \* \* \*

SEQUENCE LISTING

```
<160> NUMBER OF SEQ ID NOS: 6

<210> SEQ ID NO 1
<211> LENGTH: 1571
<212> TYPE: DNA
<213> ORGANISM: Hypocrea jecorina

<400> SEQUENCE: 1
atgcactcac gactcctcat cacggccctc ttcctgggcc tcatcgccct ggtctcggcc       60
tcggccatcc ccatccacca gaagcgcggc tccttcaagg tcgagcggag ggccaacccc      120
aacttcaccg gcaatgacgg cctcaaggcc atggccaagg cgtaccgcaa gttcggctgg      180
accatgcccc aggacctcaa ggacgcgctg gcggtgcggg aggcggccgt caaggcccgc      240
cgggctgcgg cggctgtggc tgcgcaggag gctgctgcca agaagaagag cagacgatcg      300
ctgttggatc tcctgggtga gcttggcctg ctcgggggaa acggaggcaa tggatcaaac      360
gatgatgcca atgccaatcc taacggtggc agcggaagac atcaccacgg caatggaaat      420
ggcaacggca acggcaacgg aaatggtcaa ggacaaggcc aaggccaggc tggaggaaac      480
cagactcagc ctgccccggc agcccagccc gcctctggcc aggtcggaag cgtcacaaac      540
acgcccgagg gcaacgacgt cgagttcctg tcccccgtca agatcggcgg ccagacgctc      600
aacctcgact tcgacaccgg ctcctctgac ctctgggtct tcaacacggc catggatccc      660
tcgctgacgg ccggccacac cctgtacgat cccaccaaga gcaagacctt caagcagatc      720
cagggcgcgc agttcctcgt ccagtacggc gacggctcag gcgccgaggg cgtcgtcggc      780
acggacgttg tcgacgttgg cggcgccgtc ttcgacgccc aggccgtcga gattgccacc      840
gccgtcacgc agcagtttgt cgacgaccag cagaacgacg ggctcatggg cctcgccttt      900
tccaagctca acacggtcca gccgcagcag caaaagacgt tcctcgacaa cgtccagagc      960
tccctcgccg agccgtcttt caccgccgac ctcaagaagg ccagcccgg cacgtacacc     1020 tttggcgccg tcgacgcctc cgccttccag ggcgacctga cctgggtcga cgtcgacaac     1080
tcgcagggct tctggcagtt cagcagcgag tcctttgccg tcgacggcgg cgcgacccag     1140
caggccacgg ccggcgggcca ggccattgcc gacaccggca ccaccctgct gctggccgac     1200
cccatcatcg tccagggcta ctacgcaaag gtccaggggcg cccagaacga tgcccaggcc     1260
ggtggcttta ccgtgccgtg cgatgcccag ctgcccgact ggacctggga tgttggcgga     1320
```

-continued

```
aagtatgtgg cccgcatcag cggttcggac ctcaactttg cgccggttca gggaaacagt    1380
aagttgctac cgtatcatct ttttactgag agacgacttc acaggactga cattttttcga   1440 cagcttgctt tggtggtctt caggcaacga cgcaggcggg cctgggtgtc tatggcgaca    1500
tcttcttcaa gtcgcagttt gtggcgttca acattggcaa caacacgctg ggcctggctc    1560
ctcatgctta g                                                         1571
```

```
<210> SEQ ID NO 2
<211> LENGTH: 430
<212> TYPE: PRT
<213> ORGANISM: Hypocrea jecorina

<400> SEQUENCE: 2

Met His Ser Arg Leu Leu Ile Thr Ala Leu Phe Leu Gly Leu Ile Ala
1               5                   10                  15

Leu Val Ser Ala Ser Ala Ile Pro Ile His Gln Lys Arg Gly Ser Phe
            20                  25                  30

Lys Val Glu Arg Arg Ala Asn Pro Asn Phe Thr Gly Asn Asp Gly Leu
        35                  40                  45

Lys Ala Met Ala Lys Ala Tyr Arg Lys Phe Gly Trp Thr Met Pro Gln
    50                  55                  60

Asp Leu Lys Asp Ala Leu Ala Val Arg Glu Ala Ala Val Lys Ala Arg
65                  70                  75                  80

Arg Ala Ala Ala Ala Gly Gly Asn Gln Thr Gln Pro Ala Pro Ala
                85                  90                  95

Ala Gln Pro Ala Ser Gly Gln Val Gly Ser Val Thr Asn Thr Pro Glu
            100                 105                 110

Gly Asn Asp Val Glu Phe Leu Ser Pro Val Lys Ile Gly Gly Gln Thr
            115                 120                 125

Leu Asn Leu Asp Phe Asp Thr Gly Ser Ser Asp Leu Trp Val Phe Asn
        130                 135                 140

Thr Ala Met Asp Pro Ser Leu Thr Ala Gly His Thr Leu Tyr Asp Pro
145                 150                 155                 160

Thr Lys Ser Lys Thr Phe Lys Gln Ile Gln Gly Ala Gln Phe Leu Val
                165                 170                 175

Gln Tyr Gly Asp Gly Ser Gly Ala Glu Gly Val Val Gly Thr Asp Val
            180                 185                 190

Val Asp Val Gly Gly Ala Val Phe Asp Ala Gln Ala Val Glu Ile Ala
        195                 200                 205

Thr Ala Val Thr Gln Gln Phe Val Asp Asp Gln Asn Asp Gly Leu
    210                 215                 220

Met Gly Leu Ala Phe Ser Lys Leu Asn Thr Val Gln Pro Gln Gln Gln
225                 230                 235                 240

Lys Thr Phe Leu Asp Asn Val Gln Ser Ser Leu Ala Glu Pro Val Phe
                245                 250                 255

Thr Ala Asp Leu Lys Lys Gly Gln Pro Gly Thr Tyr Thr Phe Gly Ala
            260                 265                 270

Val Asp Ala Ser Ala Phe Gln Gly Asp Leu Thr Trp Val Asp Val Asp
        275                 280                 285

Asn Ser Gln Gly Phe Trp Gln Phe Ser Ser Glu Ser Phe Ala Val Asp
    290                 295                 300

Gly Gly Ala Thr Gln Gln Ala Thr Ala Gly Gly Gln Ala Ile Ala Asp
305                 310                 315                 320

Thr Gly Thr Thr Leu Leu Leu Ala Asp Pro Ile Ile Val Gln Gly Tyr
```

-continued

```
                    325              330              335
Tyr Ala Lys Val Gln Gly Ala Gln Asn Asp Ala Gln Ala Gly Gly Phe
            340              345              350
Thr Val Pro Cys Asp Ala Gln Leu Pro Asp Leu Asp Leu Asp Val Gly
        355              360              365
Gly Lys Tyr Val Ala Arg Ile Ser Gly Ser Asp Leu Asn Phe Ala Pro
    370              375              380
Val Gln Gly Asn Thr Cys Phe Gly Gly Leu Gln Ala Thr Thr Gln Gly
385              390              395              400
Gly Leu Gly Val Tyr Gly Asp Ile Phe Phe Lys Ser Gln Phe Val Ala
            405              410              415
Phe Asn Ile Gly Asn Asn Thr Leu Gly Leu Ala Pro His Ala
            420              425              430
```

```
<210> SEQ ID NO 3
<211> LENGTH: 2388
<212> TYPE: DNA
<213> ORGANISM: Aspergillus niger

<400> SEQUENCE: 3
atgaagttct tctcgacaat ctgcagtttg acccttgcgg tctctgcgtt ggccttgcca      60
acttctgacc atgttattca tgagaagcga tctggtaccc catctcgatg ggagaagatc     120
agtcgggtca atggtactga gcatgtcttg gtgcgcatcg tctgacgca gaacaatctt      180 gatcgagcct atgagtatct catgagcgtg tatgttgctt cctcccccct atattgttcc     240
gactgactag tcaggtctga ctccgtgtcg cctaactacg gcaaattctg gactccagaa     300
gaggtgcaca gtaccttcgc gccgtcgaat gagactgtca cgctgtgcg caactggctt      360 attgaatccg gtgtggatga gtctcgcttg gttcacacca aaaaccaagg ctggattgtg     420
tttgatgcaa ccaccaaaga gcggaaaat ctcctccaca ccaagtatta ccactacaca      480
gaccggattt ctggcttcaa gacactcgca gcagaagagt atgtctccca tttattctca     540
gagatatagt atactaacaa gacgaccagg taccgcgtcc cccagaagat ccaacaacac     600
atcgacttca ttaaacccgg cgttcttctc ccattgacct ccaagggacc atccgccaag     660
cacaccaaga aatacaaacc cttgaagcag acatcagtca acgccacgtc tctcaccacg     720
tgcgacgagg tcatcactcc agcttgtgtc gccgctctgt acaagatccc tcacgcaagc     780
ggcaacgtca gtgcaagcaa ctcgcttggg atcttcgaag aaggagacta ctacgcccag     840
gaagatctgg atctcttttt ccgcaacttc accccgtaca ttccgaaggg aacacaccct     900
aagccggcat ttatcgatgg agcctcagcg cccgtgagcg ttgctgatgc tggtgcggag     960
tcggatttgg acttccagct tgcgtatcca attgtttacc ctcagaccat cacgctgtat    1020
cagacagatg actatgacta tgcgagtggg gaggttgaga ctgatggatt ctttaacacc    1080
tttcttgatg ctgttgatgg ggtaagtagc ctctggaatt ttgggattta gctaatgtct    1140
cagtcatact gcacctactg tgcctatggg gaatgcggag acagcccgac tctcgatccc    1200
acttacccag ataactccac cggaggttac aagggacagt tgatgtgcgg tgtttataag    1260
cccacgaatg tcatctccgt ttcttatggt ggccaggagg cagacctccc ggcttactac    1320
cagcagcgac aatgcaatga gtatgccatc cccacctcta tttatacagc ccgaattaac    1380
aacaggaata gattcctcaa gctcggtctc cagggcattt ccatcctctt cgcctctggc    1440
gatgacggcg tcgcagggcc cccaggcgac gactcgacta cgggtgtct gggaaatgga     1500 accatcttca gtcctgcgtt ccccaattcg tatgttttct tctcttgcaa tattcttgca    1560
```

-continued

```
acaaccacat ctaacttccc tagttgcccc tgggtgacta atgtcggagc caccaaactc    1620
taccccggaa agaccatcgc agacggggaa agcgccgtcg tcgacccggc cggccacccc    1680
tactcggtcg cattctcctc tggtggtggc ttcagcaaca tctatactat tccagactat    1740
caagccgaag cagtagcaga gtaggtgctt ttctatcatc ctatacgcgc aatctaacag    1800
cccccattca gatacttcaa aaagcacaac ccaccctatc cttactacga aggcaacgcc    1860
agcttcggca aaacggcgg tgtctacaac cgtcttggac gcgggtaccc cgacgtggca     1920
gcgaacggcg acaacatcgc cgagtacaac gcgggagaat tcatacttga gggtggaact    1980
agtgctagta cgttactacc ctactacatc cacccaactc cgttatattt caattactaa    2040
tgacaatgat taaaggtacc ccgatcttct cctccgtgat taaccgcatc atcgagaagc    2100
gaatcgcggc aggaaagggc ccactaggct tcctgaaccc ggttctgtat cggaatgcgt    2160
gggcgttgaa tgatattacg aatgggtcga atccgggttg tggaacggag gggttctata    2220
ctgctcctgg gtatgtattt ccctctcgtt tttttatttc tttattatcg tacttcgata    2280
tatggagcca tgctaacaat cggtgaacaa aatagatggg atcccgtcac cggtctcgga    2340
acgcctaact tcccgaaatt gctagacgtg ttcctgaacc tcccgtaa              2388
```

```
<210> SEQ ID NO 4
<211> LENGTH: 646
<212> TYPE: PRT
<213> ORGANISM: Aspergillus niger

<400> SEQUENCE: 4

Met Lys Phe Phe Ser Thr Ile Cys Ser Leu Thr Leu Ala Val Ser Ala
1               5                   10                  15

Leu Ala Leu Pro Thr Ser Asp His Val Ile His Glu Lys Arg Ser Gly
            20                  25                  30

Thr Pro Ser Arg Trp Glu Lys Ile Ser Arg Val Asn Gly Thr Glu His
        35                  40                  45

Val Leu Val Arg Ile Gly Leu Thr Gln Asn Asn Leu Asp Arg Ala Tyr
    50                  55                  60

Glu Tyr Leu Met Ser Val Ser Asp Ser Val Ser Pro Asn Tyr Gly Lys
65                  70                  75                  80

Phe Trp Thr Pro Glu Glu Val His Ser Thr Phe Ala Pro Ser Asn Glu
                85                  90                  95

Thr Val Asn Ala Val Arg Asn Trp Leu Ile Glu Ser Gly Val Asp Glu
            100                 105                 110

Ser Arg Leu Val His Thr Lys Asn Gln Gly Trp Ile Val Phe Asp Ala
        115                 120                 125

Thr Thr Lys Glu Ala Glu Asn Leu Leu His Thr Lys Tyr Tyr His Tyr
    130                 135                 140

Thr Asp Arg Ile Ser Gly Phe Lys Thr Leu Ala Ala Glu Glu Tyr Arg
145                 150                 155                 160

Val Pro Gln Lys Ile Gln Gln His Ile Asp Phe Ile Lys Pro Gly Val
                165                 170                 175

Leu Leu Pro Leu Thr Ser Lys Gly Pro Ser Ala Lys His Thr Lys Lys
            180                 185                 190

Tyr Lys Pro Leu Lys Gln Thr Ser Val Asn Ala Thr Ser Leu Thr Thr
        195                 200                 205

Cys Asp Glu Val Ile Thr Pro Ala Cys Val Ala Ala Leu Tyr Lys Ile
    210                 215                 220
```

-continued

```
Pro His Ala Ser Gly Asn Val Ser Ala Ser Asn Ser Leu Gly Ile Phe
225                 230                 235                 240

Glu Glu Gly Asp Tyr Tyr Ala Gln Glu Asp Leu Asp Leu Phe Phe Arg
                245                 250                 255

Asn Phe Thr Pro Tyr Ile Pro Lys Gly Thr His Pro Lys Pro Ala Phe
            260                 265                 270

Ile Asp Gly Ala Ser Ala Pro Val Ser Val Ala Asp Ala Gly Ala Glu
            275                 280                 285

Ser Asp Leu Asp Phe Gln Leu Ala Tyr Pro Ile Val Tyr Pro Gln Thr
        290                 295                 300

Ile Thr Leu Tyr Gln Thr Asp Asp Tyr Asp Tyr Ala Ser Gly Glu Val
305                 310                 315                 320

Glu Thr Asp Gly Phe Phe Asn Thr Phe Leu Asp Ala Val Asp Gly Ser
                325                 330                 335

Tyr Cys Thr Tyr Cys Ala Tyr Gly Glu Cys Gly Asp Ser Pro Thr Leu
            340                 345                 350

Asp Pro Thr Tyr Pro Asp Asn Ser Thr Gly Gly Tyr Lys Gly Gln Leu
        355                 360                 365

Met Cys Gly Val Tyr Lys Pro Thr Asn Val Ile Ser Val Ser Tyr Gly
    370                 375                 380

Gly Gln Glu Ala Asp Leu Pro Ala Tyr Tyr Gln Gln Arg Gln Cys Asn
385                 390                 395                 400

Glu Phe Leu Lys Leu Gly Leu Gln Gly Ile Ser Ile Leu Phe Ala Ser
                405                 410                 415

Gly Asp Asp Gly Val Ala Gly Pro Gly Asp Asp Ser Thr Asn Gly
                420                 425                 430

Cys Leu Gly Asn Gly Thr Ile Phe Ser Pro Ala Phe Pro Asn Ser Cys
        435                 440                 445

Pro Trp Val Thr Asn Val Gly Ala Thr Lys Leu Tyr Pro Gly Lys Thr
        450                 455                 460

Ile Ala Asp Gly Glu Ser Ala Val Val Asp Pro Ala Gly His Pro Tyr
465                 470                 475                 480

Ser Val Ala Phe Ser Ser Gly Gly Gly Phe Ser Asn Ile Tyr Thr Ile
            485                 490                 495

Pro Asp Tyr Gln Ala Glu Ala Val Ala Glu Tyr Phe Lys Lys His Asn
        500                 505                 510

Pro Pro Tyr Pro Tyr Tyr Glu Gly Asn Ala Ser Phe Gly Lys Asn Gly
        515                 520                 525

Gly Val Tyr Asn Arg Leu Gly Arg Gly Tyr Pro Asp Val Ala Ala Asn
    530                 535                 540

Gly Asp Asn Ile Ala Glu Tyr Asn Ala Gly Glu Phe Ile Leu Glu Gly
545                 550                 555                 560

Gly Thr Ser Ala Ser Thr Pro Ile Phe Ser Ser Val Ile Asn Arg Ile
            565                 570                 575

Ile Glu Lys Arg Ile Ala Ala Gly Lys Gly Pro Leu Gly Phe Leu Asn
        580                 585                 590

Pro Val Leu Tyr Arg Asn Ala Trp Ala Leu Asn Asp Ile Thr Asn Gly
        595                 600                 605

Ser Asn Pro Gly Cys Gly Thr Glu Gly Phe Tyr Thr Ala Pro Gly Trp
    610                 615                 620

Asp Pro Val Thr Gly Leu Gly Thr Pro Asn Phe Pro Lys Leu Leu Asp
625                 630                 635                 640

Val Phe Leu Asn Leu Pro
```

645

<210> SEQ ID NO 5
<211> LENGTH: 1302
<212> TYPE: DNA
<213> ORGANISM: Hypocrea jecorina

<400> SEQUENCE: 5
atgcagacct ttggagcttt tctcgtttcc ttcctcgccg ccagcggcct ggccgcggcc        60
ctccccaccg agggtcagaa gacggcttcc gtcgaggtcc agtacaacaa gaactacgtc       120
ccccacggcc ctactgctct cttcaaggcc aagagaaagt atggcgctcc catcagcgac       180
aacctgaagt ctctcgtggc tgccaggcag gccaagcagg ctctcgccaa cgcgccagacc     240 ggctcggcgc ccaaccaccc cagtgacagc gccgattcgg agtacatcac ctccgtctcc       300
atcggcactc cggctcaggt cctccccctg actttgaca ccggctcctc cgacctgtgg        360
gtctttagct ccgagacgcc caagtcttcg gccaccggcc acgccatcta cacgccctcc       420
aagtcgtcca cctccaagaa ggtgtctggc ccagctggt ccatcagcta cggcgacggc       480
agcagctcca gcggcgatgt ctacaccgac aaggtcacca tcggaggctt cagcgtcaac       540
acccagggcg tcgagtctgc caccccgcgtg tccaccgagt tcgtccagga cacggtcatc      600
tctggcctcg tcggccttgc ctttgacagc ggcaaccagg tcaggccgca cccgcagaag       660
acgtggttct ccaacgccgc cagcagcctg gctgagcccc ttttcactgc cgacctgagg       720
cacggacaga gtaagtagac actcactgga attcgttcct ttcccgatca tcatgaaagc       780
aagtagactg actgaaccaa caactagac ggcagctaca actttggcta catcgacacc        840
agcgtcgcca agggccccgt tgcctacacc cccgttgaca cagccagggg cttctgggag       900
ttcactgcct cgggctactc tgtcggcggc ggcaagctca accgcaactc catcgacggc       960
attgccgaca ccggcaccac cctgctcctc ctcgacgaca acgtcgtcga tgcctactac      1020
gccaacgtcc agtcggccca gtacgacaac cagcaggagg gtgtcgtctt cgactgcgac      1080
gaggacctcc cttcgttcag cttcggtgtt ggaagctcca ccatcaccat ccctggcgat      1140
ctgctgaacc tgactcccct cgaggagggc agctccacct gcttcggtgg cctccagagc      1200
agctccggca ttggcatcaa catctttggt gacgttgccc tcaaggctgc cctggttgtc      1260
tttgacctcg caacgagcg cctgggctgg gctcagaaat aa                          1302

<210> SEQ ID NO 6
<211> LENGTH: 407
<212> TYPE: PRT
<213> ORGANISM: Hypocrea jecorina

<400> SEQUENCE: 6

Met Gln Thr Phe Gly Ala Phe Leu Val Ser Phe Leu Ala Ala Ser Gly
1               5                   10                  15

Leu Ala Ala Ala Leu Pro Thr Glu Gly Gln Lys Thr Ala Ser Val Glu
            20                  25                  30

Val Gln Tyr Asn Lys Asn Tyr Val Pro His Gly Pro Thr Ala Leu Phe
        35                  40                  45

Lys Ala Lys Arg Lys Tyr Gly Ala Pro Ile Ser Asp Asn Leu Lys Ser
    50                  55                  60

Leu Val Ala Ala Arg Gln Ala Lys Gln Ala Leu Ala Lys Arg Gln Thr
65                  70                  75                  80

Gly Ser Ala Pro Asn His Pro Ser Asp Ser Ala Asp Ser Glu Tyr Ile
            85                  90                  95

-continued

```
Thr Ser Val Ser Ile Gly Thr Pro Ala Gln Val Leu Pro Leu Asp Phe
            100             105             110

Asp Thr Gly Ser Ser Asp Leu Trp Val Phe Ser Ser Glu Thr Pro Lys
            115             120             125

Ser Ser Ala Thr Gly His Ala Ile Tyr Thr Pro Ser Lys Ser Ser Thr
            130             135             140

Ser Lys Lys Val Ser Gly Ala Ser Trp Ser Ile Ser Tyr Gly Asp Gly
145             150             155             160

Ser Ser Ser Ser Gly Asp Val Tyr Thr Asp Lys Val Thr Ile Gly Gly
                165             170             175

Phe Ser Val Asn Thr Gln Gly Val Glu Ser Ala Thr Arg Val Ser Thr
            180             185             190

Glu Phe Val Gln Asp Thr Val Ile Ser Gly Leu Val Gly Leu Ala Phe
            195             200             205

Asp Ser Gly Asn Gln Val Arg Pro His Pro Gln Lys Thr Trp Phe Ser
            210             215             220

Asn Ala Ala Ser Ser Leu Ala Glu Pro Leu Phe Thr Ala Asp Leu Arg
225             230             235             240

His Gly Gln Asn Gly Ser Tyr Asn Phe Gly Tyr Ile Asp Thr Ser Val
                245             250             255

Ala Lys Gly Pro Val Ala Tyr Thr Pro Val Asp Asn Ser Gln Gly Phe
                260             265             270

Trp Glu Phe Thr Ala Ser Gly Tyr Ser Val Gly Gly Gly Lys Leu Asn
            275             280             285

Arg Asn Ser Ile Asp Gly Ile Ala Asp Thr Gly Thr Thr Leu Leu Leu
            290             295             300

Leu Asp Asp Asn Val Val Asp Ala Tyr Tyr Ala Asn Val Gln Ser Ala
305             310             315             320

Gln Tyr Asp Asn Gln Gln Glu Gly Val Val Phe Asp Cys Asp Glu Asp
                325             330             335

Leu Pro Ser Phe Ser Phe Gly Val Gly Ser Ser Thr Ile Thr Ile Pro
            340             345             350

Gly Asp Leu Leu Asn Leu Thr Pro Leu Glu Glu Gly Ser Ser Thr Cys
            355             360             365

Phe Gly Gly Leu Gln Ser Ser Ser Gly Ile Gly Ile Asn Ile Phe Gly
    370             375             380

Asp Val Ala Leu Lys Ala Ala Leu Val Val Phe Asp Leu Gly Asn Glu
385             390             395             400

Arg Leu Gly Trp Ala Gln Lys
                405
```